US010772862B2

(12) United States Patent
Rabinowitz et al.

(10) Patent No.: US 10,772,862 B2
(45) Date of Patent: Sep. 15, 2020

(54) LIPID SCAVENGING IN RAS CANCERS

(71) Applicants: Memorial Sloan Kettering Cancer Center, New York, NY (US); The Trustees of Princeton University, Princeton, NJ (US)

(72) Inventors: Joshua Rabinowitz, Princeton, NJ (US); Jurre Kamphorst, Glasgow (GB); Craig Thompson, New York, NY (US); Justin Cross, New York, NY (US)

(73) Assignees: The Trustees of Princeton University, Princeton, NJ (US); Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/160,237

(22) Filed: Oct. 15, 2018

(65) Prior Publication Data
US 2019/0046489 A1   Feb. 14, 2019

Related U.S. Application Data

(62) Division of application No. 14/890,106, filed as application No. PCT/US2014/037514 on May 9, 2014, now Pat. No. 10,130,600.

(60) Provisional application No. 61/822,095, filed on May 10, 2013.

(51) Int. Cl.
| | | |
|---|---|---|
| *A61K 31/20* | (2006.01) | |
| *A61K 45/06* | (2006.01) | |
| *A61K 31/202* | (2006.01) | |
| *G01N 33/574* | (2006.01) | |
| *A23L 33/10* | (2016.01) | |
| *A23L 33/115* | (2016.01) | |
| *A23L 33/12* | (2016.01) | |
| *A23L 33/17* | (2016.01) | |
| *A61K 31/685* | (2006.01) | |
| *A61K 31/66* | (2006.01) | |
| *A61K 36/889* | (2006.01) | |

(52) U.S. Cl.
CPC .............. *A61K 31/20* (2013.01); *A23L 33/10* (2016.08); *A23L 33/115* (2016.08); *A23L 33/12* (2016.08); *A23L 33/17* (2016.08); *A61K 31/202* (2013.01); *A61K 45/06* (2013.01); *G01N 33/5748* (2013.01); *A23V 2002/00* (2013.01); *A61K 31/66* (2013.01); *A61K 31/685* (2013.01); *A61K 36/889* (2013.01); *G01N 2500/10* (2013.01); *G01N 2800/52* (2013.01)

(58) Field of Classification Search
CPC ...................................................... A61K 31/20
USPC ............................................................ 514/558
See application file for complete search history.

(56) References Cited

U.S. PATENT DOCUMENTS

| 6,214,875 | B1 | 4/2001 | Yang | |
|---|---|---|---|---|
| 7,569,350 | B2 | 8/2009 | Gocke et al. | |
| 10,130,600 | B2 | 11/2018 | Rabinowitz et al. | |
| 2006/0217441 | A1 | 9/2006 | Akimoto et al. | |
| 2010/0129430 | A1* | 5/2010 | Sofou ............... | A61K 9/1271 424/450 |
| 2016/0120832 | A1 | 5/2016 | Rabinowitz et al. | |

FOREIGN PATENT DOCUMENTS

| CA | 2140866 A1 | 2/1994 |
|---|---|---|
| CA | 2688293 A1 | 12/2008 |
| WO | WO-1994/002108 A1 | 2/1994 |
| WO | WO-2006/065735 A1 | 6/2006 |
| WO | WO-2012/165345 A1 | 12/2012 |
| WO | WO-2012/172411 A1 | 12/2012 |
| WO | WO-2014/183047 A1 | 11/2014 |

OTHER PUBLICATIONS

Han et al., "Fish Oil Inhibits Human Lung Carcinoma Cell Growth by Suppressing Integrin-Linked Kinase", Molecular Cancer Research, vol. 7, No. 1, pp. 108-117 (2009).*
Zhang et al., "Modulatory Effects of EPA and DHA on Proliferation and Apoptosis of Pancreatic Cancer Cells", Journal of Huazhong University of Science and Technology, Medical Science, vol. 27, No. 5, pp. 547-550 (2007).*
Reddy, "Omega-3 Fatty Acids in Colorectal Cancer Prevention", International Journal of Cancer, vol. 112, No. 1, pp. 1-7 (2004).*
Bar-Sagi, D. and Feramisco, J.R., Induction of membrane ruffling and fluid-phase pinocytosis in quiescent fibroblasts by Ras proteins, Science, 233(4768):1061-1068 (1986).
Bradley, M.G. et al., Non-steroidal anti-inflammatory drugs and pancreatic cancer risk: a nested case-control study, British Journal of Cancer, 102: 1415-1421 (2010).
Chun, S. Y. et al, Oncogenic KRAS modulates mitochondrial metabolism in human colon cancer cells by inducing HIF-1α and HIF-2α target genes, Mol. Cancer, 9(293): 1-11 (2010).
Commisso, C. et al., Macropinocytosis of protein is an amino acid supply route in Ras-transformed cells, Nature, 497(7451): 633-637 (2013).
Deberardinis, R.J. et al, Brick by brick: metabolism and tumor cell growth, Curr. Opin. Genet. Dev., 18(1):54-61 (2008).
Degenhardt, K. & White, E., A mouse model system to genetically dissect the molecular mechanisms regulating tumorigenesis, Clin. Cancer Res., 12(18):5298-5304 (2006).
Degenhardt, K. et al, BAX and BAK mediate p53-independent suppression of tumorigenesis, Cancer Cell, (2):193-203 (2002).

(Continued)

*Primary Examiner* — Kevin E Weddington
(74) *Attorney, Agent, or Firm* — Brenda Herschbach Jarrell; David E. Shore; Choate, Hall & Stewart LLP

(57) ABSTRACT

Methods and compositions for treating Ras-related cancers are provided that involve targeting lipid scavenging. Methods and compositions for identifying and/or characterizing more or less responsive cancers are also provided.

17 Claims, 12 Drawing Sheets

(56) References Cited

OTHER PUBLICATIONS

Funahashi, H. et al., Opposing effects of n-6 and n-3 polyunsaturated fatty acids on pancreatic cancer growth, Pancreas, 36(4): 353-62 (2008).
Gaglio, D. et al., Oncogenic K-Ras decouples glucose and glutamine metabolism to support cancer cell growth, Molecular Systems Biology, 7(523): 1-15 (2011).
Gingras, A-C. et al, Regulation of translation initiation by FRAP/mTOR, Genes & Development 15:807-826 (2001).
Green, C.D. and Olson, L.K., Modulation of palmitate-induced endoplasmic reticulum stress and apoptosis in pancreatic β-cells by stearoyl-CoA desaturase and ElovI6, Am. J. Physiol Endocrinol Metab., 300: E640-E649 (2011).
Guillou, H. et al., The key roles of elongases and desaturases in mammalian fatty acid metabolism: insights from transgenic mice, Prog Lipid Res, 49(2):186-199 (2010).
Guo, J.Y., et al, Activated Ras requires autophagy to maintain oxidative metabolism and tumorigenesis, Genes & Development, 25:460-470 (2011).
Hardy, S. et al, Oleate Activates Phosphatidylinositol 3-Kinase and Promotes Proliferation and Reduces Apoptosis of MDA-MB-231 Breast Cancer Cells, Whereas Palmitate Has Opposite Effects, Cancer Research, 60: 6353-6358 (2000).
Hess, D. et al, Inhibition of StearoylCoA Desaturase Activity Blocks Cell Cycle Progression and Induces Programmed Cell Death in Lung Cancer Cells, PLOS One 5(6):e11394 (2010).
Hu, Y. et al, K-ras$^{G12v}$ transformation leads to mitochondrial dysfunction and a metabolic switch from oxidative phosphorylation to glycolysis, Cell Research, 22(2):399-412 (2012).
Igal, A.R., Roles of StearoylCoA Desaturase-1 in the Regulation of Cancer Cell Growth, Survival and Tumorigenesis, Cancers, 3: 2462-2477 (2011).
International Search Report of PCT/US2014/037514, 3 pages (dated Oct. 14, 2014).
Joyce, T. et al., A molecular signature for epithelial to mesenchymal transition in a human colon cancer cell system is revealed by large-scale microarray analysis, Clin Exp Metastasis, 26(6):569-587 (2009).
Kalaany, N.Y. and Sabatini, D.M., Tumours with PI3K activation are resistant to dietary restriction, Nature 458(7239): 725-732 (2009).
Kamphorst et al., Hypoxic and Ras-transformed cells support growth by scavenging unsaturated fatty acids from lysophospholipids, PNAS, 1 0(22): 8882-8887 (2013).
Kamphorst et al., Liquid Chromatography High Resolution Mass Spectrometry Analysis of Fatty Acid Metabolism, Anal. Chem., 83: 9114-9122 (2011).
Kamphorst et al., Ras-driven cancer cells can scavenge exogenous lipids to support their proliferation, BMC Proceedings, 6(Suppl. 3): 1-2 (2012).
Kannan, R. et al, Dietary Control of Lipogenesis in vivo in Host Tissues and Tumors of Mice Bearing Ehrlich Ascites Carcinoma, Cancer Research, 40:4606-4611 (1980).
Khwaja, A. et al., Matrix adhesion and Ras transformation both activate a phosphoinositide 3-OH kinase and protein kinase B/Akt cellular survival pathway, The EMBO Journal, 16(10): 2783-2793 (1997).
Kim, J-W. et al, HIF-1-mediated expression of pyruvate dehydrogenase kinase: A metabolic switch required for cellular adaptation to hypoxia, Cell Metabolism,(3):177-185 (2006).
Krypuy, M. et al, High resolution melting analysis for the rapid and sensitive detection of mutations in clinical samples: KRAS codon 12 and 13 mutations in non-small cell lung cancer, BMC Cancer, 6:295-307 (2006).
Li, C. et al, Prevention of carcinogenesis and inhibition of breast cancer tumor burden by dietary stearate, Carcinogenesis, 32(8): 1251-8 (2011).
Li, H. et al, High-throughput screening for fatty acid uptake inhibitors in humanized yeast identifies atypical antipsychotic drugs that cause dyslipidemias, J. Lipid Res., 49(1): 230-44 (2008).
Lu, W. et al, Metabolomic analysis via reversed-phase ion-pairing liquid chromatography coupled to a stand alone orbitrap mass spectrometer, Anal. Chem., 82(8): 3212-3221 (2010).
Luyimbazi, D. et al, Rapamycin regulates Stearoyl CoA Desaturase 1 Expression in Breast Cancer, Mol. Cancer Ther., 9(10):2770-2784 (2010).
Mason, P. et al, SCD1 Inhibition Causes Cancer Cell Death by Depleting Mono-Unsaturated Fatty Acids, PLOS One, 7(3):e33823 (2012).
Menendez, J.A. and Lupu, R., Fatty acid synthase and the lipogenic phenotype in cancer pathogenesis, Nat Rev Cancer, 7(10):763-777 (2007).
Metallo, C.M. et al, Reductive glutamine metabolism by IDH1 mediates lipogenesis under hypoxia, Nature, 481(7381):380-384 (2011).
Miyazaki, M. et al, Stearoyl-CoA desaturase-1 deficiency attenuates obesity and insulin resistance in leptin-resistant obese mice, Biochem Biophys Res. Commun., 380(4): 818-822 (2009).
Mullen, A.R. et al, Reductive carboxylation supports growth in tumour cells with defective mitochondria, Nature 481(7381):385-388 (2011).
Nicolaou, K.C. et al., Calicheamicin θ11: A rationally designed molecule with extremely potent and selective DNA cleaving properties and apoptosis inducing activity, Angew Chem Intl Ed Engl, 33:183-186 (1994).
Nomura, D.K. et al, Monoacylglycerol lipase regulates a fatty acid network that promotes cancer pathogenesis, Cell, 140(1): 49-61 (2010).
Papandreou, I. et al, HIF-1 mediates adaptation to hypoxia by actively downregulating mitochondrial oxygen consumption, Cell Metabolism, 3:187-197 (2006).
Roongta et al., Cancer cell dependence on unsaturated fatty acids implicates stearoyl-CoA desaturase as a target for cancer therapy, Mol. Cancer Red. 9: 1551-1561 (2011).
Santos, C. R. and Schulze, A., Lipid metabolism in cancer, the FEBS Journal minireview, 279: 2610-2623 (2012).
Sasagawa, T. et al., Abnormal serum lysophospholipids in multiple myeloma patients, Lipids, 34(1):17-21 (1998).
Schulze, A. and Harris, A.L., How cancer metabolism is tuned for proliferation and vulnerable to disruption, Nature, 491:364-373 (2012).
Shaw, R.J. Aand Cantley, L.C., Ras, PI(3)K and mTOR signaling controls tumour cell growth, Nature, 441:424-430 (2006).
Sheta, E.A. et al, Cell density mediated pericellular hypoxia leads to induction of HIF-1alpha via nitric oxide and Ras/MAP kinase mediated signaling pathways, Oncogene, 20:7624-7634 (2001).
Therasse, P. et. al., New guidelines to evaluate the response to treatment in solid tumors, European Organization for Research and Treatment of Cancer, National Cancer Institute of the United States, National Cancer Institute of Canada, J. Natl. Cancer Inst., 92(3):205-216 (2000).
Vander Heiden, M.G. et al, Understanding the Warburg Effect: The Metabolic Requirements of Cell Proliferation, Science, 324(5930):1029-1033 (2009).
White, E., Exploiting the bad eating habits of Ras-driven cancers, Genes and Dev., 27: 2065-2071 (2013).
Wise, D.R. et al, Hypoxia promotes isocitrate dehydrogenase-dependent carboxylation of α-ketoglutarate to citrate to support cell growth and viability, Proc. Natl. Acad. Sci., 108(49):19611-19616 (2011).
Written Opinion of PCT/US2014/037514, 9 pages (dated Oct. 14, 2014).
Yang, S. et al, Pancreatic cancers require autophagy for tumor growth, Genes & Development, 25:717-729 (2011).
Ying, H. et al, Oncogenic Kras Maintains Pancreatic Tumors through Regulation of Anabolic Glucose Metabolism, Cell, 149(3): 656-670 (2012).

\* cited by examiner

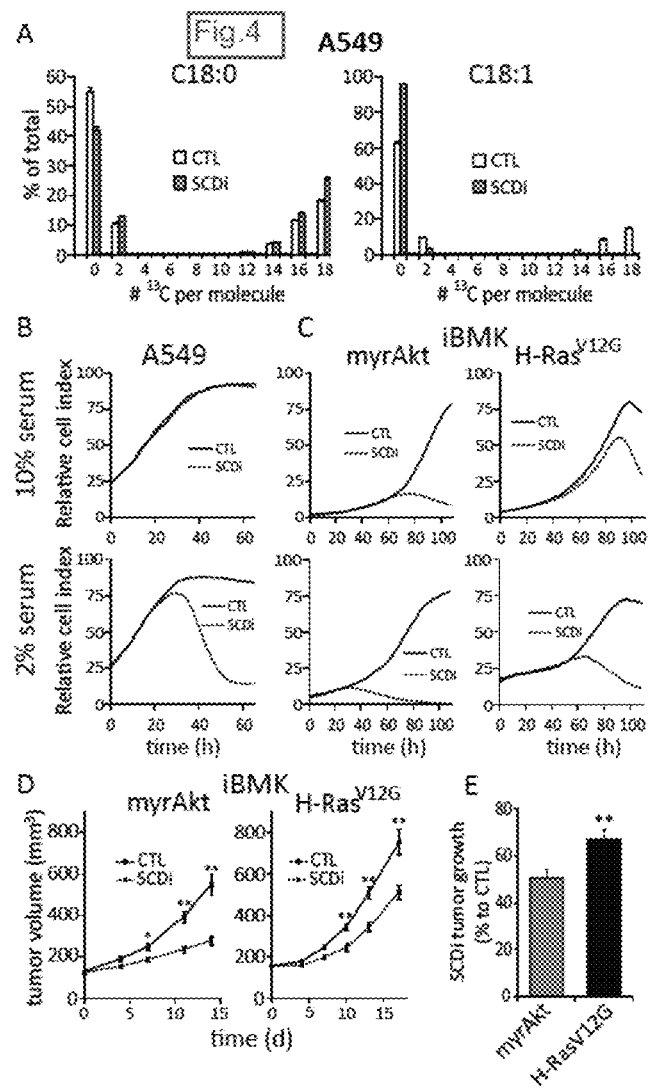

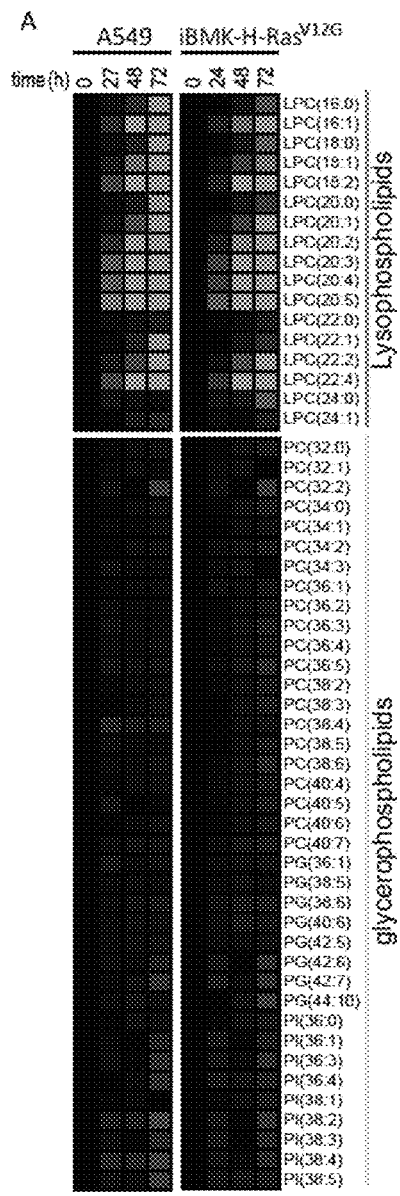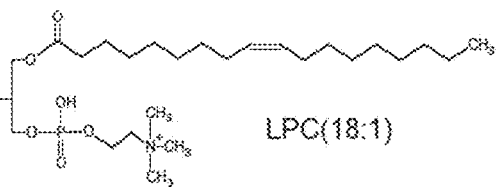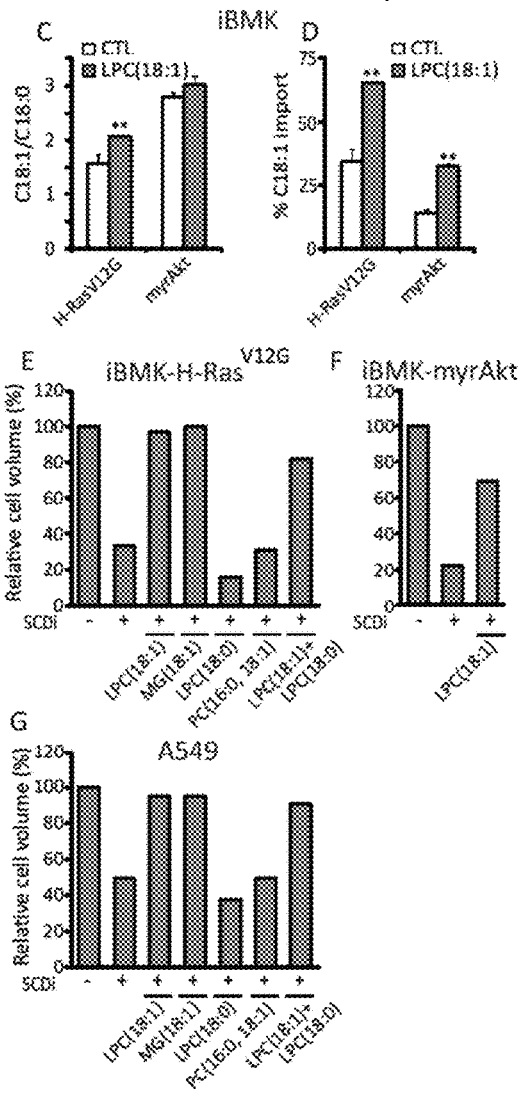

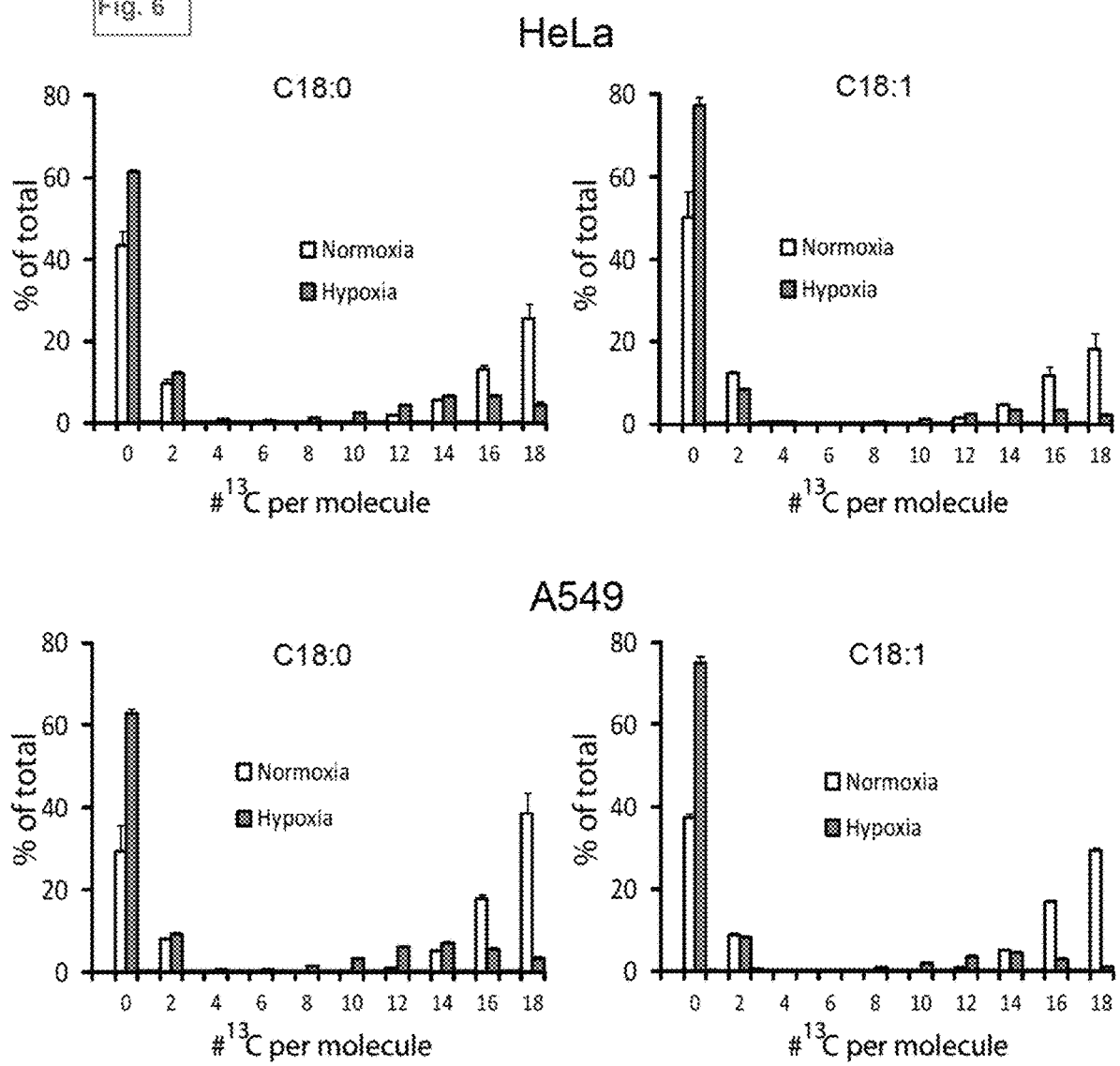

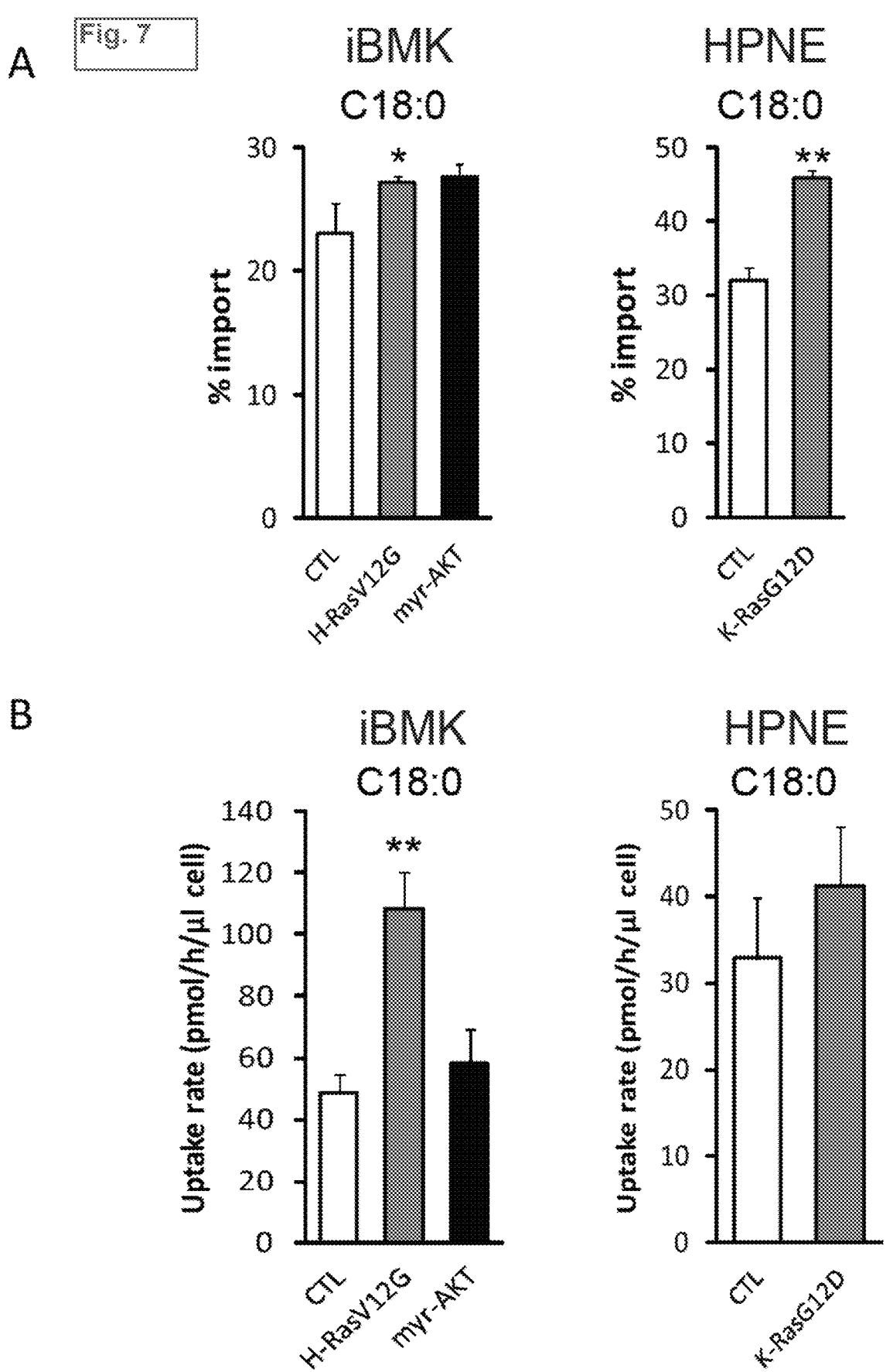

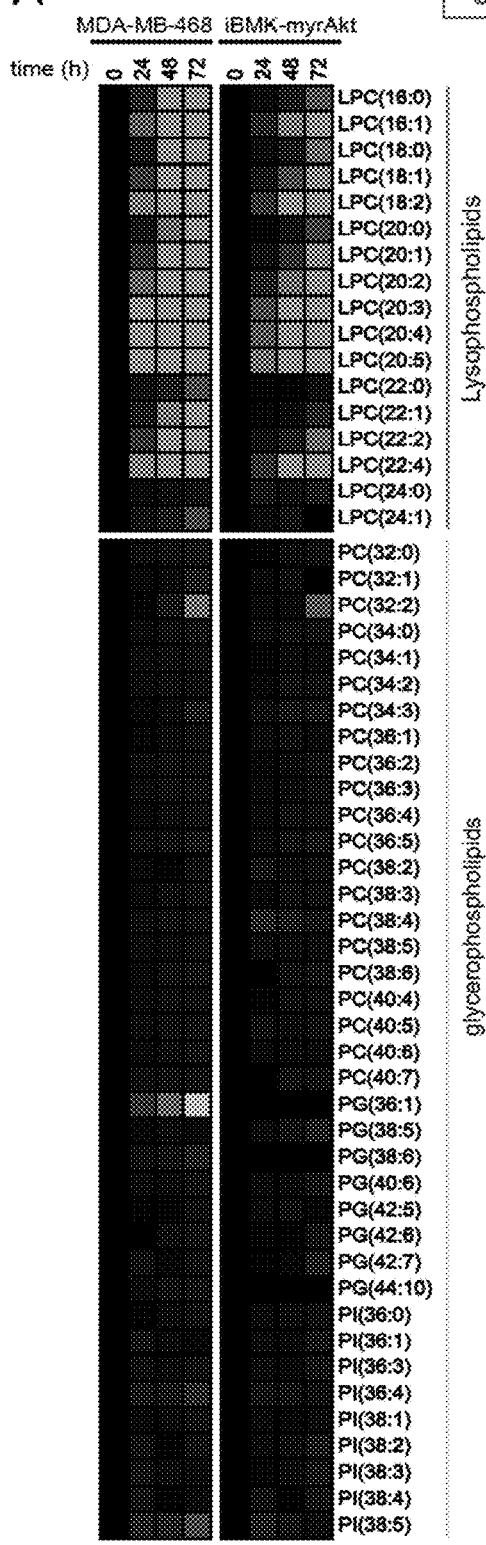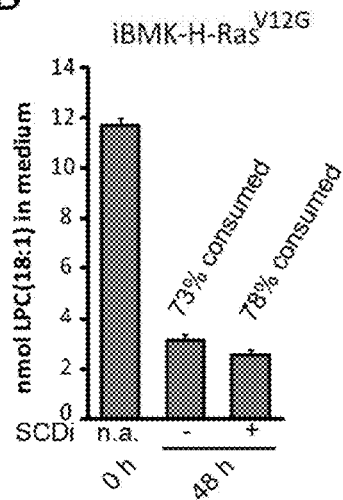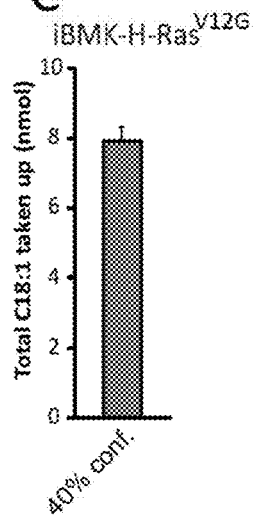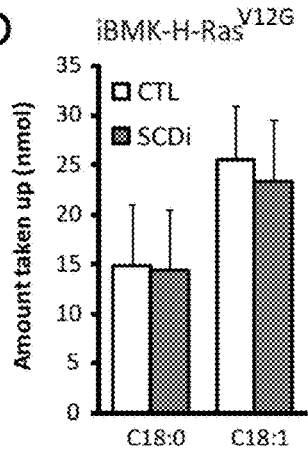
Fig. 10

LIPID SCAVENGING IN RAS CANCERS

RELATED APPLICATIONS

This application is a divisional of U.S. patent application Ser. No. 14/890,106, which is a national stage entry of PCT/US2014/037514, filed on May 9, 2014, which claims the benefit of U.S. Provisional Patent Application No. 61/822,095, filed on May 10, 2013, the contents of which are herein incorporated by reference in their entirety.

GOVERNMENT SUPPORT

This invention was made with government support under grant numbers: CA163591, CA108438 and CA105463 awarded by the National Institutes of Health. The government has certain rights in the invention.

BACKGROUND

Cancer cells require a constant supply of energy and structural components to support proliferation. Many cancer cells have been shown to have high rates of de novo lipid synthesis (see, for example, Santos & Schulze *FEBS J* MiniReview 279(15):2610, Jul. 3, 2012). Recently, several therapeutic development strategies have focused on inhibitors of lipid biosynthesis for treatment of cancer.

Two of the most commonly activated pathways in human cancer are the PI3K-Akt and the Ras pathways. The metabolic effects of the PI3K-Akt pathway have been extensively studied, as, in addition to its role in cancer, this pathway is the primary effector of insulin signaling. Akt activation promotes glucose uptake, glycolytic flux, and lactate excretion, i.e., the Warburg effect. In addition, through downstream activation of mTOR, it increases protein synthesis. Finally, Akt induces lipogenesis through mechanisms including enzyme phosphorylation and transcriptional activation, like mTOR-dependent activation of SREBP.

Fatty acids are a primary component of lipids. Their synthesis requires the generation of cytosolic acetyl-CoA (FIG. 1A). In normoxia, a predominant pathway involves catabolism of glucose to pyruvate, which is converted to mitochondrial acetyl-CoA by pyruvate dehydrogenase. Acetyl-CoA is then exported to the cytosol in the form of citrate, which is cleaved to generate cytosolic acetyl-CoA by ATP-citrate lyase, a direct Akt target. In hypoxia, pyruvate dehydrogenase is inactivated by pyruvate dehydrogenase kinase, and glutamine-driven reductive carboxylation accounts for an increased fraction of citrate and thus acetyl-CoA.

Subsequent steps in the fatty acid synthesis pathway are catalyzed by acetyl-CoA carboxylase and fatty acid synthase, which are SREBP targets, and yield palmitate (C16:0, where 16 refers to the number of carbon atoms in the fatty acid, and zero to the number of double bonds). Palmitate in turn is a substrate for various elongation and desaturation reactions to accommodate a cell's need for a diversity of fatty acids, of which the most abundant is the monounsaturated fatty acid oleate (C18:1). Oleate is produced from palmitate by elongation to stearate (C18:0) followed by desaturation by $\Delta 9$ stearoyl-CoA desaturase 1 (SCD1), which requires oxygen as an electron acceptor. A specific ratio of oleate to stearate must be maintained by cells to ensure proper membrane fluidity and thus cell integrity, and a significant imbalance has been shown to induce apoptosis. SCD1 is regulated by the PI3K-Akt-mTOR pathway and has been investigated as a pharmacological target for both obesity and cancer.

Like PI3K-Akt pathway activation, Ras activation induces glucose uptake and lactate excretion. While Ras is known to activate the PI3K-Akt pathway, recent findings suggest that downstream metabolic effects may diverge. For example, Ras reduces mitochondrial respiration. In addition, Ras induces macropinocytosis and autophagy, thereby providing potential alternative sources of metabolic substrates. In further support of a divergent metabolic effect, mouse xenograft experiments revealed a difference in sensitivity to caloric restriction between Ras-driven tumors and tumors with PI3K-Akt activation. In contrast to the pro-lipogenic effect of Akt, the impact of Ras on lipid metabolism has not been investigated. Moreover, the interplay of oxygen availability and oncogene signaling on metabolism, including lipid metabolism, has not been extensively explored.

The foregoing observations provide evidence of the continuing need for compositions and formulations useful in treating Ras-driven cancers.

SUMMARY

The present disclosure specifically encompasses the recognition that hypoxic cells bypass de novo lipogenesis, and thus both the need for acetyl-CoA and the oxygen-dependent SCD1-reaction, by scavenging serum fatty acids, and furthermore that hypoxic reprogramming of de novo lipogenesis can be reproduced in normoxic cells by Ras activation. The present disclosure therefore demonstrates that Ras-driven cells, including for example Ras-driven tumors, may show resistance to SCD1 inhibition. Moreover, the present disclosure demonstrates that Ras-driven cells, including for example Ras-driven tumors, may show susceptibility to therapeutic regimens that reduce their successful lipid scavenging.

The present disclosure specifically demonstrates that preferred substrates for lipid scavenging by hypoxic and/or Ras-driven cells include phospholipids with one fatty acid tail (lysophospholipids). The present disclosure demonstrates that Ras-driven cells, including for example Ras-driven tumors, may show susceptibility to therapeutic regimens that reduce their successful scavenging of lysophospholipids.

$^{13}$C-tracers and lipidomics were used to study lipogenesis in transformed cells as a function of oncogene expression and oxygen availability. It was found that hypoxia reduces the requirement for de novo fatty acid synthesis and desaturation by increasing fatty acid import. Oncogenic Ras recapitulates the hypoxic metabolic phenotype, and the increased reliance on fatty acid uptake renders Ras-driven cancer cells resistant to SCD1 inhibition. A major source of the imported fatty acids are serum lipids with one fatty acid tail, lysolipids. The ability to catabolize lipids with a single fatty acid tail was previously shown to be enhanced in aggressive and Ras-driven cancers. The present results show that related scavenging of lysolipids can be a major route of fatty acid acquisition in both hypoxia and Ras-driven cancer cells.

The present disclosure also specifically demonstrates that phosphatidylglycerol lipids and/or fatty acids with higher degrees of unsaturation and/or longer carbon chains were typically detectable at higher levels in tumors (e.g., Ras-associated tumors) than in adjacent benign tumors. The present disclosure demonstrates that Ras-driven cells, including for example Ras-driven tumors, may show susceptibility to therapeutic regimens that reduce their successful scavenging of such phosphatidylglycerol lipids and/or fatty acids with higher degrees of unsaturation.

In one aspect, the present disclosure specifically provides modalities for reducing successful lipid scavenging by Ras-driven cells (e.g., Ras-associated tumors) by controlling levels and/or types of scavenged lipids in serum, for example through dietary control of lipid intake. In some embodiments, lipid intake is controlled by limiting intake of favored scavenged lipids. In some embodiments, lipid intake is controlled by regulating relative intake of favored scavenged lipids as compared with other lipids. In some particular embodiments, lipid intake is controlled through provision and/or use of a nutritional supplement comprising lipids, and particular contain lipids that are not favored scavenged lipids for the cells or tumors of interest.

In many embodiments, dietary control for reducing lipid scavenging, e.g., by Ras-driven control, comprises consuming or administering a diet with an excess of fully saturated fatty acids. In some embodiments, such dietary control is or comprises use of nutritional supplements comprising or consisting of such fully saturated fatty acids.

To give but one example, in some embodiments, a nutritional supplement, food substitute, or dietary regimen is provided or utilized wherein the ratio of saturated fatty acids to polyunsaturated fatty acids in the supplement is greater than 1.

In some embodiments, the ratio of saturated fatty acids to polyunsaturated fatty acids is greater than 2, 3, 4, 5, 8, 10, 15, 20, 25, 30, 35, 40, 45, or 50.

In some embodiments, a nutritional supplement, food substitute, or dietary regimen comprises less than 10%, 9%, 8%, 7%, 6%, 5%, 4%, 3%, 3%, or preferably less than 1%, 0.9%, 08%, 0.7%, 0.6%, 0.5%, 0.4%, or 0.3% by weight of essential fatty acids.

In some embodiments, a nutritional supplement, food substitute, or dietary regimen includes an arachidonic acid concentration less than 0.1% by weight.

In some embodiments, at least 70% of a nutritional supplement or food substitute by weight is lipid.

In some embodiments, utilized lipid is derived from animal and/or plant sources. In some embodiments, utilized lipid is derived from coconut.

In some embodiments, utilized lipid is derived from land animal or dairy sources.

In some embodiments, a nutritional supplement, food substitute, or dietary regimen further comprises a protein source.

In some embodiments, a nutritional supplement, food substitute, or dietary regimen further comprises a carbohydrate source.

In some embodiments, a nutritional supplement or food substitute is in the form of a pill or capsule.

In another aspect, there is provided a method of treating cancer comprising administering to a patient in need thereof a diet comprising a ratio of saturated fatty acids to polyunsaturated fatty acids greater than 1.

In some embodiments, the ratio of saturated fatty acids to polyunsaturated fatty acids greater than 2, 3, 4, 5, 8, 10, 15, 20, 25, 30, 35, 40, 45, or 50.

In some embodiments, the cancer is a Ras-driven cancer. In some embodiments, the Ras-driven cancer is selected from the group consisting of pancreatic cancer, non-small-cell lung cancer, colorectal cancer, bladder cancer, kidney cancer, thyroid cancer, melanoma, hepatocellular carcinoma, and hematologic malignancies.

In some embodiments, the diet is administered over a time period of at least 2 weeks. In some embodiments, the diet is administered over a time period of 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed.

In some embodiments, the saturated fatty acids are from animal and/or plant sources. In some embodiments, the saturated fatty acids are derived from coconut. In some embodiments, the saturated fatty acids are derived from land animal or dairy sources.

In some embodiments, the method further comprises administering a chemotherapeutic agent.

In another aspect of the disclosure, there is provided a method of treating cancer comprising administering to a patient in need thereof one or more pharmacological inhibitors of cancer cell growth and instructing the patient to consume a diet that limits intake of favored scavenged lipids, for example by consuming a diet comprising a ratio of saturated fatty acids to polyunsaturated fatty acids greater than 1.

In another aspect of the disclosure, there is provided a method of treating cancer comprising administering to a patient in need thereof a diet comprising any of the nutritional supplements described herein.

In another aspect of the disclosure, there is provided a method of treating cancer comprising administering to a patient in need thereof one or more pharmacological inhibitors of cancer cell growth and instructing the patient to consume a diet comprising any of the nutritional supplements described herein.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTION OF THE DRAWING

FIG. 4. Differential impact of Ras and Akt on sensitivity to SCD1 inhibition. (A) 200 nM CAY10566 (SCD1 inhibitor, SCDi) blocks C18:1 labeling from U-$^{13}$C-glucose and U-$^{13}$C-glutamine. (B, C) Impact of SCDi on A549, iBMK-H-Ras$^{V12G}$, and iBMK-myrAkt cell growth in xCELLigence instrument. CTL is vehicle control. (D) Growth of allografted iBMK-H-Ras$^{V12G}$ and iBMK-myrAkt tumors treated with vehicle (CTL) or SCDi (CAY10566, 2.5 mg/kg BID p.o.). (E) Percentage growth of iBMK-H-Ras$^{V12G}$ and iBMK-myrAkt tumors relative to untreated controls, after 13 and 14 days treatment with SCDi, respectively. For panels A-C, data are mean±SD of N≥3. For panels (D-E) data are mean±SEM of N=10 mice per group. *$p<0.05$; **$p<0.01$ (two-tailed T-test).

FIG. 5. Fatty acids are scavenged from lysophospholipids. (A) Fold changes in medium phospholipids during growth of A549 and iBMK-H-Ras$^{V12G}$ cells (relative to fresh medium with 10% serum). (B) Structure of LPC(18:1). (C) Effect of LPC(18:1) supplementation (20 μM, 72 h) on desaturation index (C18:1/C18:0) and (D) Percent contribution of import to the cellular C18:1 pool based on U-$^{13}$C-glucose and U-$^{13}$C-glutamine labeling in iBMK-H-Ras$^{V12G}$ and iBMK-myrAkt cells. (E-G) Packed cell volume for (E) iBMK-H-Ras$^{V12G}$, (F) iBMK-myrAkt, and (G) A549 cells (relative to untreated control, CTL) after 72 h incubation with or without 200 nM SCDi (CAY10566), in the presence of the indicated supplemented lipids (20 μM), LPC, lysophosphatidylcholine; PC, phosphatidylcholine; PG, phosphatidylglycerol; PI, phosphatidylinositol; MG, monoacylglycerol. Data are (A) mean N=3; (C-D) mean±SD of N=3; (E-G) mean N=2. *$p<0.05$; **$p<0.01$ (two-tailed T-test).

FIG. 6. Fatty acid labeling in normoxia and hypoxia. Labeling patterns of stearate (C18:0) and oleate (C18:1) from saponified cellular lipid extracts from cells grown in U-$^{13}$C-glucose and U-$^{13}$C-glutamine, in normoxia and hypoxia (1% $O_2$ for HeLa, and 0.5% for A549) for 72 h. All data are mean±SD of N=3.

FIG. 7. Effect of oncogenic Ras on de novo synthesis versus import of stearate (C18:0). (A) Percent import of C18:0, as measured by fatty acid labeling (72 h) from U-$^{13}$C-glucose and U-$^{13}$C-glutamine, in immortalized baby mouse kidney (iBMK) isogenic cell lines engineered to express myrAkt or H-Ras$^{V12G}$ versus vector control (CTL), and HPNE cells with oncogenic K-Ras$^{G12D}$ versus vector control (CTL). (B) Uptake rates of C18:0, based on measurements of saponified lipids from fresh and spent medium (10% serum, 72 h incubation). All data are mean±SD of N≥3. *$p<0.05$; **$p<0.01$ (two-tailed T-test).

FIG. 10. Lysophospholipid consumption by cancer cells. (A) Fold changes in medium phospholipids during growth of MDA-MB-468 and iBMK-myrAkt cells (relative to fresh medium with 10% serum). (B) Consumption (in nmol) of LPC(18:1) from medium by iBMK-H-Ras$^{V12G}$ cells treated with 200 nM CAY10566 (SCD1 inhibitor, SCDi) or vehicle control (CTL), for 48 h. (C) Total C18:1 import (based on uptake rates from FIG. 3C) for cells cultured to ~40% confluence. (D) Effect of SCDi inhibition on total C18:1 uptake, based on measurements of saponified lipids from fresh and spent medium (10% serum, 48 h incubation). Cells were seeded at higher density than usual to facilitate optimal determination of fatty acid consumption. All data are mean±SD of N≥3.

DEFINITIONS

Figure 1:
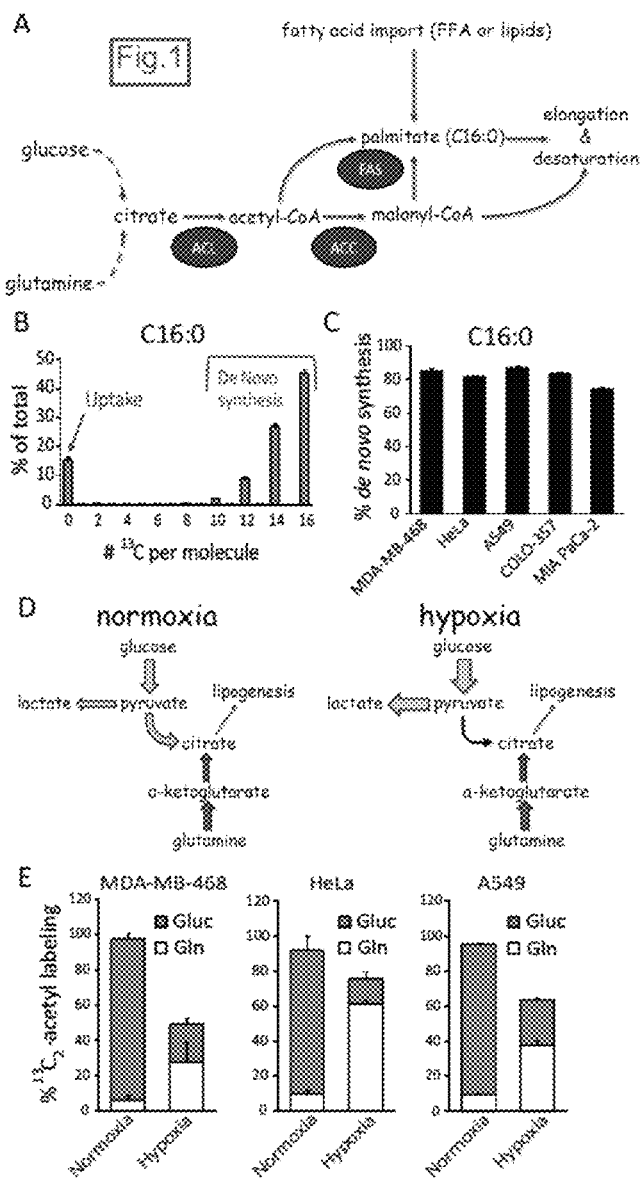
FIG. 1. Palmitate is mainly synthesized from glucose in normoxia, with increased fractional contribution from glutamine in hypoxia. (A) Schematic representation of de novo palmitate (C16:0) synthesis; ACL, ATP-citrate lyase; ACC, acetyl-CoA carboxylase; FAS, fatty acid synthase; FFA, free fatty acids. (B) Labeling pattern of palmitate (C16:0) saponified from cellular lipids, from MDA-MB-468 cells grown in U-$^{13}$C-glucose and U-$^{13}$C-glutamine for >5 doublings. (C) Percent cellular palmitate (C16:0) fatty acid tails acquired through de novo synthesis, based on $^{13}$C-labeling patterns as per (B). (D) Schematic of the contribution of glucose and glutamine to lipogenesis in normoxia and hypoxia. (E) Percent labeling of acetyl groups from U-$^{13}$C-glucose (Gluc) and U-$^{13}$C-glutamine (Gln) in normoxia and hypoxia (1% $O_2$). Acetyl labeling from N-acetyl-glutamate and glutamate at steady-state; analysis of fatty acid labeling gives equivalent results. All data are mean±SD of N=3.
Figure 2:
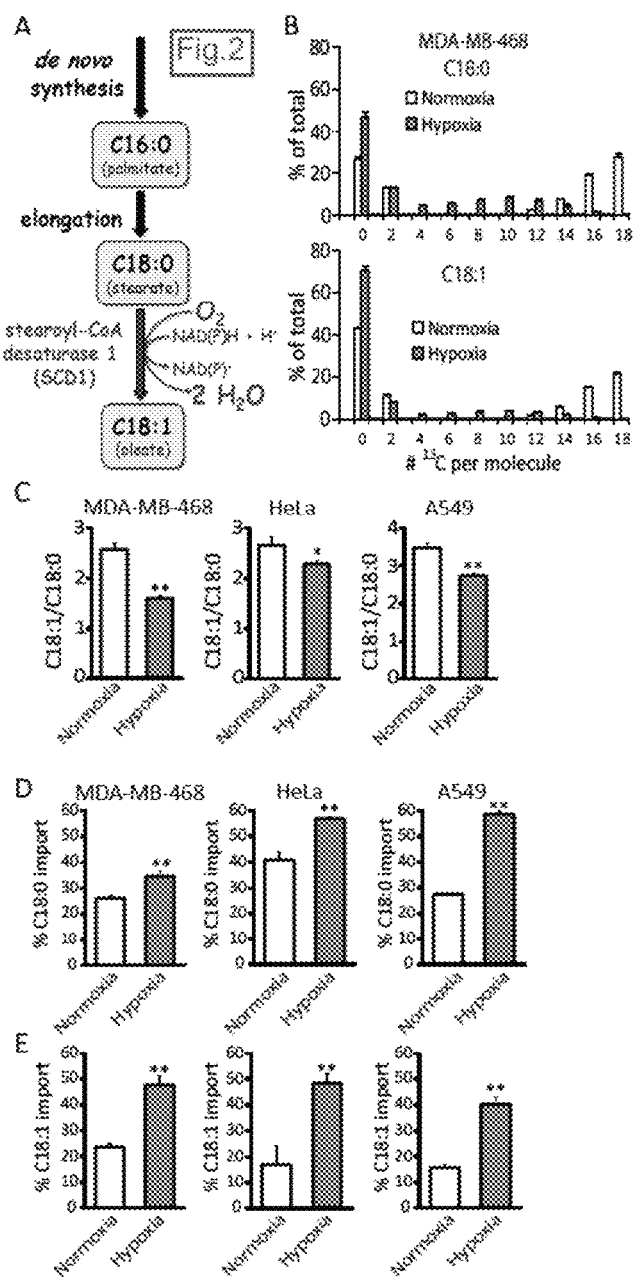
FIG. 2. Hypoxia decreases SCD1 flux and increases fatty acid import. (A) Schematic of oleate (C18:1) synthesis. (B) Labeling patterns of C18:0 and C18:1 from MDA-MB-468 cells grown in U-$^{13}$C-glucose and U-$^{13}$C-glutamine, in normoxia and hypoxia (1% $O_2$) for 72 h. (C) Desaturation index (C18:1/C18:0) in normoxia and hypoxia (1% $O_2$ for MDA-MB-468 and HeLa cells, and 0.5% for A549 cells). (D-E) Percent import of C18:0 (D) and C18:1 (E) pools in normoxia and hypoxia, as measured by fatty acid labeling for 72 h, from U-$^{13}$C-glucose and U-$^{13}$C-glutamine. All data are mean±SD of N=3. *$p<0.05$; **$p<0.01$ (two-tailed T-test).
Figure 3:
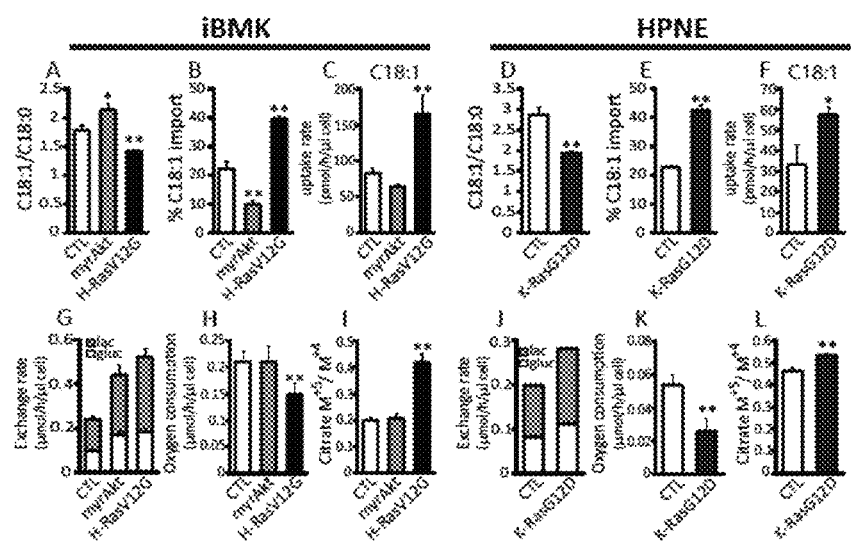
FIG. 3. Oncogenic Ras mimics hypoxia, increasing fatty acid scavenging and acetyl-CoA labeling from glutamine and decreasing oxygen consumption. (A) Desaturation index (C18:1/C18:0) in immortalized baby mouse kidney (iBMK) isogenic cell lines engineered to express myrAkt or H-Ras$^{V12G}$ versus vector control (CTL). (B) Percent import of C18:1, as measured by steady-state fatty acid labeling from U-$^{13}$C-glucose and U-$^{13}$C-glutamine. (C) Uptake rates of C18:1, based on measurements of saponified lipids from fresh and spent medium (10% serum, 72 h incubation). (D, E, F) Same measurements for HPNE cells with oncogenic K-Ras$^{G12D}$ versus vector control (CTL). (G) Glucose uptake and lactate excretion in iBMK cells; lac, lactate; gluc, glucose. (H) Oxygen consumption. (I) Ratio of citrate produced from reductive carboxylation of glutamine-derived α-ketoglutarate (M$^{+5}$) to oxidative metabolism (M$^{+4}$). (J, K, L) Same measurements in HPNE cells. All data are mean±SD of N≥3. *$p<0.05$; **$p<0.01$ (two-tailed T-test).
Figure 8:
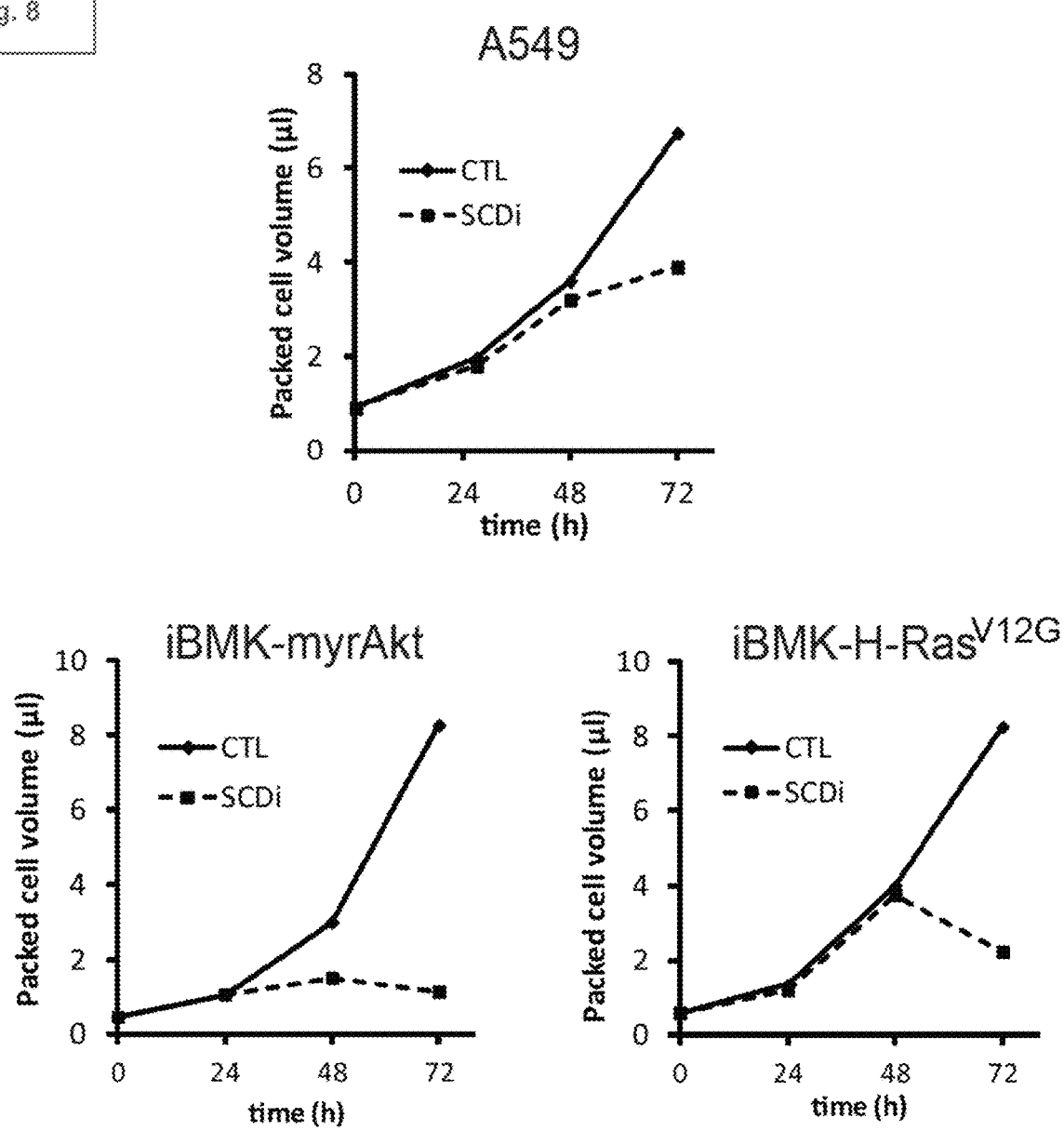
FIG. 8. Effect of SCD1 inhibition on cell growth in 6 cm tissue culture dishes. Onset of growth inhibition, upon treatment with 200 nM CAY10566, occurs earlier in the tissue culture dishes than when using the xCELLigence system where growth is on 96-well culture plates, because the cells grow faster and therefore more rapidly consume medium lipids on the 6 cm dishes. Mean N=2.
Figure 9:
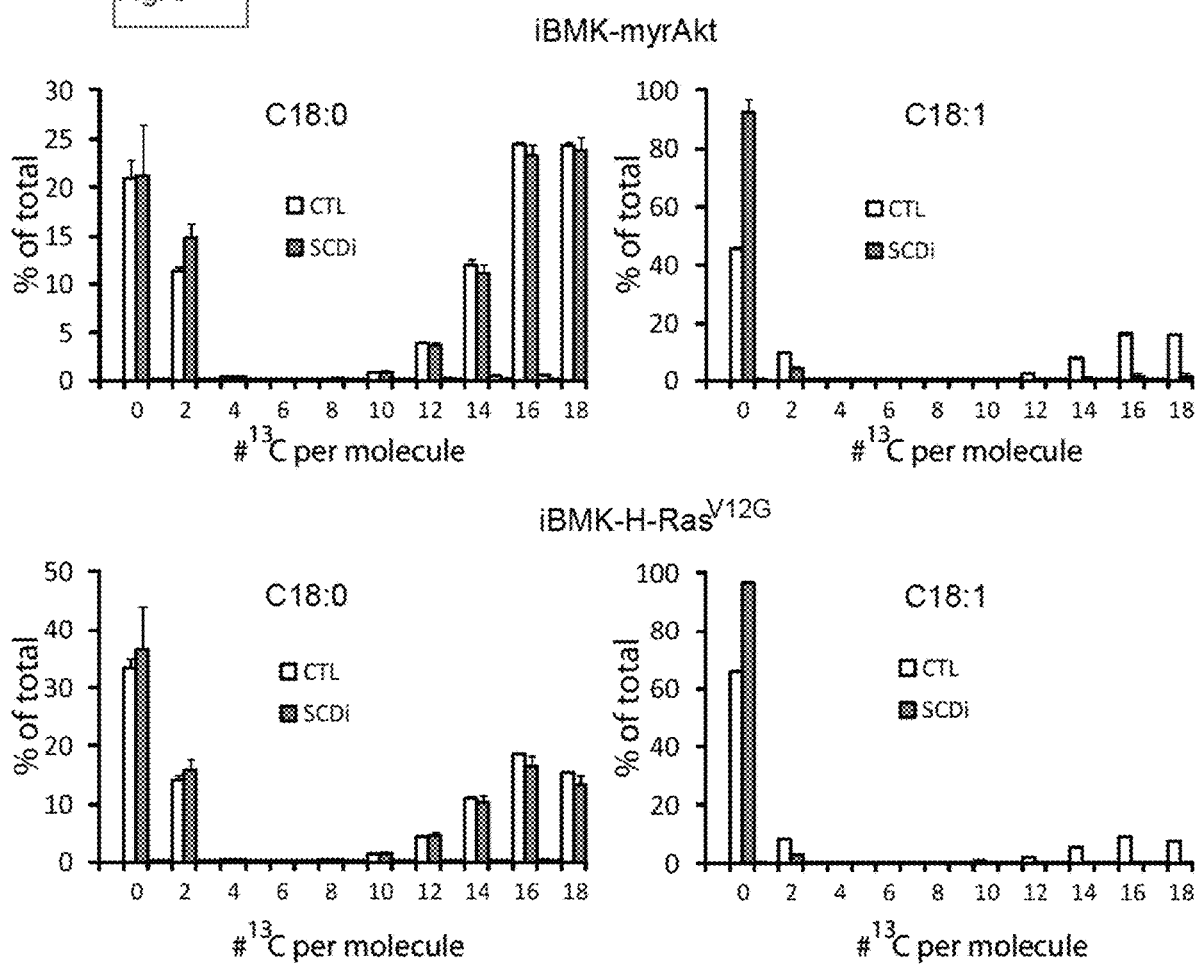
FIG. 9. 200 nM CAY10566 is sufficient to fully block C18:1 labeling. Cells were treated with 200 nM CAY10566 (SCD1 inhibitor, SCDi) or vehicle control (CTL) while cultured in medium with U-$^{13}$C-glucose and U-$^{13}$C-glutamine for 48 h. All data are mean±SD of N≥3.

Activating agent: As used herein, the term "activating agent" refers to an agent whose presence or level correlates with elevated level or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Agent: The term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antagonist: As used herein, the term "antagonist" refers to an agent that i) inhibits, decreases or reduces the effects of another agent; and/or ii) inhibits, decreases, reduces, or delays one or more biological events. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon its target) or indirect (in which case it exerts its influence by other than binding to its target; e.g., by interacting with a regulator of the target, for example so that level or activity of the target is altered).

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Characteristic portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity.

In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Comparable: The term "comparable", as used herein, refers to two or more agents, entities, situations, sets of conditions, etc that may not be identical to one another but that are sufficiently similar to permit comparison therebetween so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" is often used to designate a structural element or moiety in an agent of interest that shares a position (e.g., in three-dimensional space or relative to another element or moiety) with one present in an appropriate reference agent. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition (such as cancer), state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modalitiy such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Essential fatty acid: As used herein, the term "essential fatty acids" refers to a fatty acid that a particular organism (e.g., human) must ingest because the body requires them for good health but cannot synthesize them. Exemplary essential fatty acids include, but are not limited to, omega-6 fatty acid and omega-3 fatty acid.

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Modulator: The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent.

In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Ras-associated: As used herein, the term "Ras-associated" or "Ras-driven" is used to refer to cells or tumors in which the Ras oncogene is activated (e.g., is increased in expression and/or activity relative to an appropriate control cell or tissue, such as a comparable, including an otherwise identical, cell or tissue that is not cancerous for example in that it is not characterized by unregulated or otherwise increased proliferation and/or contains or expresses a Ras allele or mutation that is associated or correlated with activation). In some embodiments, such Ras activation is detected in the tumor. In some embodiments, the tumor is of a type, or is progeny of a type, for which a correlation with Ras activation has been established.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Risk: As will be understood from context, a "risk" of a disease, disorder or condition is a degree of likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

Specific: The term "specific", when used herein with reference to an agent or entity having an activity, is understood by those skilled in the art to mean that the agent or entity discriminates between potential targets or states. For example, an agent is said to bind "specifically" to its target if it binds preferentially with that target in the presence of competing alternative targets. In some embodiments, the agent or entity does not detectably bind to the competing alternative target under conditions of binding to its target. In some embodiments, the agent or entity binds with higher on-rate, lower off-rate, increased affinity, decreased dissociation, and/or increased stability to its target as compared with the competing alternative target(s).

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen", as that term is used herein, refers to a dosing regimen whose administration across a relevant population is correlated with a desired or beneficial therapeutic outcome.

Therapeutically effective amount: As used herein, the term "therapeutically effective amount" refers to an amount of a therapeutic protein (e.g., receptor tyrosine kinases antibody) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., anti-receptor tyrosine kinases antibodies or receptor tyrosine kinase antagonists) that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION OF CERTAIN EMBODIMENTS

Lipid Metabolism in Cancer

Cancer cells require a constant supply of energy and structural components to support their proliferation. Oncogenes actively reprogram metabolism to facilitate this supply (1, 2). Two of the most commonly activated pathways in human cancer are the PI3K-Akt and the Ras pathways (3). The metabolic effects of the PI3K-Akt pathway have been extensively studied, as, in addition to its role in cancer, this pathway is the primary effector of insulin signaling. Akt activation promotes glucose uptake, glycolytic flux, and lactate excretion, i.e., the Warburg effect (2). In addition, through downstream activation of mTOR, it increases protein synthesis (4). Finally, Akt induces lipogenesis through mechanisms including enzyme phosphorylation and transcriptional activation, like mTOR-dependent activation of SREBP (5, 6).

Fatty acids are a primary component of lipids. Their synthesis requires the generation of cytosolic acetyl-CoA (FIG. 1A). In normoxia, a predominant pathway involves catabolism of glucose to pyruvate, which is converted to mitochondrial acetyl-CoA by pyruvate dehydrogenase. Acetyl-CoA is then exported to the cytosol in the form of citrate, which is cleaved to generate cytosolic acetyl-CoA by ATP-citrate lyase, a direct Akt target. In hypoxia, pyruvate dehydrogenase is inactivated by pyruvate dehydrogenase kinase (7, 8), and glutamine-driven reductive carboxylation accounts for an increased fraction of citrate and thus acetyl-CoA (9-11).

Subsequent steps in the fatty acid synthesis pathway are catalyzed by acetyl-CoA carboxylase and fatty acid synthase, which are SREBP targets, and yield palmitate (C16:0, where 16 refers to the number of carbon atoms in the fatty acid, and zero to the number of double bonds). Palmitate in turn is a substrate for various elongation and desaturation reactions to accommodate a cell's need for a diversity of fatty acids, of which the most abundant is the monounsaturated fatty acid oleate (C18:1) (12). Oleate is produced from palmitate by elongation to stearate (C18:0) followed by desaturation by $\Delta 9$ stearoyl-CoA desaturase 1 (SCD1), which requires oxygen as an electron acceptor. A specific ratio of oleate to stearate must be maintained by cells to ensure proper membrane fluidity and thus cell integrity, and a significant imbalance has been shown to induce apoptosis (13-15). SCD1 is regulated by the PI3K-Akt-mTOR pathway (5) and has been investigated as a pharmacological target for both obesity and cancer (16-19).

Indeed, prior to the present disclosure, and as discussion in the Examples included herein, prior to the present disclosure, it has been commonly assumed that cancer cells synthesize most of their non-essential fatty acids de novo. This assumption is based primarily on cell culture experiments conducted in 10% serum and normoxia. It is supported by the glucose-dependent pro-lipogenic effects of one of the most important oncogenic pathways, PI3K-Akt-mTOR. Because Ras activates Akt, the expectation has been that Ras might also have a glucose-dependent pro-lipogenic role. The present disclosure demonstrates, among other things, the source of a problem with such assumptions.

Like PI3K-Akt pathway activation, Ras activation induces glucose uptake and lactate excretion (20). While Ras is known to activate the PI3K-Akt pathway, the present disclosure appreciates that recent findings suggest that downstream metabolic effects may diverge. For example, Ras reduces mitochondrial respiration (21). In addition, Ras induces macropinocytosis and autophagy, thereby providing potential alternative sources of metabolic substrates (22-24). In further support of a divergent metabolic effect, mouse xenograft experiments revealed a difference in sensitivity to caloric restriction between Ras-driven tumors and tumors with PI3K-Akt activation (25). In contrast to the prolipogenic effect of Akt, the impact of Ras on lipid metabolism had not previously been investigated. Moreover, the interplay of oxygen availability and oncogene signaling on metabolism, including lipid metabolism, had not been extensively explored prior to the present disclosure.

As described herein, we used $^{13}C$-tracers and lipidomics to study lipogenesis in transformed cells as a function of oncogene expression and oxygen availability. We found that hypoxia reduces the requirement for de novo fatty acid synthesis and desaturation by increasing fatty acid import. Oncogenic Ras recapitulates the hypoxic metabolic phenotype, and the increased reliance on fatty acid uptake renders Ras-driven cancer cells resistant to SCD1 inhibition. A major source of the imported fatty acids are serum lipids with one fatty acid tail, lysolipids. The ability to catabolize lipids with a single fatty acid tail was previously shown to be enhanced in aggressive and Ras-driven cancers (26-28). The present results show that related scavenging of lysolipids can be a major route of fatty acid acquisition in both hypoxia and Ras-driven cancer cells.

Thus, the present disclosure demonstrates that Ras does not induce glucose-dependent de novo lipogenesis, but instead stimulates scavenging of serum fatty acids. Such scavenging is an intrinsic property of all cells studied herein, and is further increased by Ras activation, hypoxia, and/or addition to media of physiological concentrations of lysophospholipid (i.e., phospholipids with only one fatty acid tail). Enhanced scavenging renders Ras-driven cells resistant to pharmacological inhibition of the main mammalian desaturase, SCD1. Moreover, it may facilitate the growth of Ras-driven tumors in hypoxic conditions by circumventing SCD1, which requires molecular oxygen as an electron acceptor.

Targeting Lipid Scavenging

The present disclosure demonstrates the value of and provides a variety of technologies for targeting lipid scavenging, particularly in tumor cells such as, for example, in Ras-associated tumors. In some embodiments, such targeting permits identification of cells (e.g., tumor cells) and/or tumors that are successfully scavenging lipids from their environment. In some embodiments, provided technologies can identify and/or characterize degree and/or kind of lipid scavenging and/or relative reliance on lipid scavenging as compared with lipid biosynthesis. Such technologies therefore permit identification of cells and/or tumors whose growth, proliferation, and/or viability may be impacted by modifying lipid scavenging systems.

To give but a few examples, as will be clear to those skilled in the art reading the present disclosure, lipid scavenging cells and/or tumors are less susceptible to growth inhibition with modalities that inhibit lipid synthesis; by contrast, such cells and/or tumors are more susceptible to growth inhibition with modalities that interfere with lipid scavenging. In some embodiments, therefore, the present invention provides technologies for classifying cells and/or tumors as relatively likely or unlikely to respond to different types of therapy. For example, in accordance with the present invention, lipid scavenging cells are less likely to respond to therapy that inhibits or disrupts lipid biosynthesis, and are more likely to respond to therapy that inhibits or disrupts lipid scavenging. Alternatively or additionally, in some embodiments, the present invention provides technologies for selecting appropriate therapeutic modalities for treatment of particular tumors, and/or for treating such tumors with such modalities.

In some embodiments, the present invention provides technologies for targeting lipid scavenging by modulating presence or level of scavengeable lipids from the cellular milleu. For example, as described herein, lipid scavenging tumor cells, such as Ras-associated tumor cells, tend to preferentially accumulate phospholipids with one fatty acid tail (lysophospholipids). The present disclosure demonstrates that Ras-driven cells, including for example Ras-driven tumors, may show susceptibility to therapeutic regimens that reduce their successful scavenging of lysophospholipids, including, for example, by restricting levels of such lysophospholipids in the cellular milleu (e.g., in blood).

The present disclosure also specifically demonstrates that phosphatidylglycerol lipids and/or fatty acids with higher degrees of unsaturation and/or longer carbon chains were often detectable at higher levels in tumors (e.g., Ras-associated tumors) than in adjacent benign tumors. The present disclosure demonstrates that Ras-driven cells, including for example Ras-driven tumors, may show susceptibility to therapeutic regimens that reduce their successful scavenging of such lipids (e.g., phosphatidylglycerol lipids and/or fatty acids with higher degrees of unsaturation and/or longer carbon tails). The present disclosure demonstrates that Ras-driven cells, including for example Ras-driven tumors, may show susceptibility to therapeutic regimens that reduce their successful scavenging of such lipids, including, for example, by restricting their levels in the cellular milleu (e.g., in blood).

In some embodiments, the present invention provides technologies for targeting lipid scavenging by exposing cells (e.g., tumor cells and/or tumors) to conditions and/or agents that inhibit level and/or activity of one or more agents that participates in and/or is required for successful scavenging of one or more lipids. Alternatively or additionally, in some embodiments, the present invention provides technologies for targeting lipid scavenging by exposing cells (e.g., tumor cells and/or tumors) to conditions and/or agents that enhance level and/or activity of one or more agents that interferes with (including, for example, by direct inhibition, by competition, and/or by diversion) successful scavenging of one or more lipids.

In some embodiments, a relevant agent interacts directly with a component of cellular lipid scavenging machinery. In some embodiments, a relevant agent does not interact directly with a component of cellular lipid scavenging machinery.

Susceptible Tumors

Among other things, the present disclosure demonstrates that certain Ras-associated tumors utilize and/or rely on lipid scavenging. Such tumors are therefore likely, in accordance with the present invention, to be relatively less likely to respond to therapeutic modalities that inhibit or disrupt lipid biosynthesis, and relatively more likely to respond to therapeutic modalitieis that inhibit or disrupt lipid scavenging.

The uptake and utilization of lysophospholipids by Ras-driven cells is part of a more global "scavenger" mode of existence. Oncogenic Ras up-regulates both autophagy and macropinocytosis, both involving uptake of bulk material into endocytotic vesicles. The former consumes intracellular contents (cellular cannibalism) and the latter extracellular ones. Both can provide nutrition via macromolecule degradation, and it is possible that macropinocytosis contributes directly to lysolipid uptake.

Irrespective of a potential role for macropinocytosis, scavenging is a metabolic hallmark of Ras driven cancers. While tumors driven by the PI3K-Akt pathway aggressively engage in biosynthesis and become metabolically vulnerable, the present disclosure demonstrates that those driven primarily by oncogenic Ras instead have the capacity to maintain rapid growth by utilizing extracellular macromolecules to obtain the required substrates for new macromolecule and lipid production. This observation has therapeutic implications, rendering Ras driven tumors comparatively robust to inhibitors of anabolic enzymes such as SCD1. At the same time, it implicates scavenging pathway enzymes as therapeutic targets for Ras-driven cancers.

Ras is a family of related proteins called small GTPase, and are involved in transmitting signals within cells (cellular signal transduction). Exemplary Ras proteins include, but are not limited to, H-Ras, N-Ras and K-Ras. All Ras proteins function as binary signaling switches with "on" and "off" states. Typically, in the "off" state (or deactivated state), it is bound to the nucleotide guanosine diphosphate (GDP); while in the "on" state (or activated state), Ras is bound to guanosine triphosphate (GTP). Normally, Ras is regulated by cycling between the active GTP-bound and inactive GDP-bound forms. As used herein, the term "chronically activated Ras" refers to a Ras GTPase form that is constitutively or permanently locked in an active state or has reduced deactivation rate as compared to a wild type Ras.

Typically, a chronically activated Ras contains a mutation that prevents or reduces the rate of GTP hydrolysis. In some embodiments, a chronically activated Ras is caused by mutations found at residue G12 in the P-loop and/or the catalytic residue Q61. For example, the glycine to valine mutation at residue 12 of H-Ras results chronically activated Ras. As another non-limiting example, residue 61 is responsible for stabilizing the transition state for GTP hydrolysis. In some embodiments, a chronically active Ras contains a Q61K mutation in N-Ras, which reduces the rate of intrinsic Ras GTP hydrolysis. As another non-limiting example, mutations in codon 12 (Gly to Ala, Arg, Asp, Cys, Ser, or Val) and codon 13 (Gly to Asp) result in chronically activated K-Ras.

Particular Ras alleles known to be associated with Ras activation include, for example: H-RasV12G, K-RasG12D, and K-RasG12V.

Chronically activated Ras has been implicated in various cancers. For example, the following cancers are known to be associated with chronically activated Ras: lung cancer K-Ras, pancreas (K-Ras), non-small cell lung adenocarcinoma (K-Ras), colorectal (K-Ras), thyroid (K-Ras, H-Ras and N-Ras), seminoma (K-Ras and N-Ras), myelodysplastic syndrome (K-Ras and N-Ras), acute myeloid leukemia (N-Ras), chronic myeloid leukemia (N-Ras), melanoma (N-Ras), bladder (H-Ras), liver (N-Ras) and kidney (H-Ras), to name but a few.

The below Table provides a more comprehensive, though not necessarily complete, list of Ras-associated cancers:

TABLE 1

Exemplary Ras-associated Cancers

| Defect or mutation | Tumor Type | Frequency (%) |
|---|---|---|
| RAS - K | Pancreas | 90 |
| RAS - K | Lung adenocarcinoma (non-small cell) | 35 |
| RAS - K | Colorectal | 45 |
| RAS - H, K, N | Thyroid (Follicular) | 55 |
| RAS - H, K, N | Thyroid (Undifferentiated papillary) | 60 |
| RAS - K, N | Seminoma | 45 |
| RAS - N, K | Myelodysplastic syndrome | 40 |
| RAS - N | Acute myelogenous leukaemia | 30 |
| RAS - N | Melanoma | 15 |
| RAS - H | Bladder | 10 |
| RAS - N | Liver | 30 |
| RAS - H | Kidney | 10 |
| RAS - K | Lung adenocarcinoma | 33 |
| RAS - K | Colon adenocarcinoma | 44, 40, 47 (different methods) |
| RAS - K | Colon adenoma | 50 |
| RAS - K | Colon adenoma (familial adenomatous polyposis) | 13, 7 |
| RAS - K | Pancreas (adenocarcinoma) | 84, 93, 75 (diff. methods) |
| RAS - H, K, N | Thyroid (Follicular carcinoma) | 53 |
| RAS - H, K, N | Thyroid (Undifferentiated carcinoma) | 60 |
| RAS - K, N | Seminoma | 43 |
| RAS - N, K | Myelodysplastic syndrome | 5, 38, 40, 41, 9 |
| RAS - N | Acute myeloid leukaemia | 50, 63, 19, 27, 19, 56, 70, 28, 27, 26, 26, 11 |
| RAS - N | Chronic myeloid leukaemia | 17 (chronic), 50 (acute) |
| RAS - N | Melanoma | 8, 19 |
| RAS - H | Bladder carcinoma | 7, 7, 17 (diff methods) |
| RAS - N | Liver carcinoma | 30 |
| RAS - H | Kidney carcinoma | 16, 14 |

Targeting Agents

In principle, any agent whose level, form, and/or activity correlates with and/or modulates (e.g., inhibits or enhances) a feature of lipid scavenging can be a lipid scavenging targeting agent, at least for certain embodiments as described herein.

In some embodiments, an agent that targets lipid scavenging as described herein is or comprises a small molecule. In some embodiments, an agent that targets lipid scavenging as described herein is or comprises a polypeptide. In some embodiments, an agent that targets lipid scavenging as described herein is or comprises a nucleic acid. In some embodiments, an agent that targets lipid scavenging as described herein is or comprises a glycan. In some embodiments, an agent that targets lipid scavenging as described herein is or comprises a lipid.

In some embodiments, an agent that targets lipid scavenging as described herein is or comprises an antibody agent (e.g., that binds to a component of the lipid scavenging machinery).

In some embodiments, an agent that targets lipid scavenging as described herein is or comprises a nucleic acid agent (e.g., an antisense or siRNA agent) (e.g., that binds to a component of the lipid scavenging machinery and/or to a gene or gene product that encodes it or is complimentary such.

In some embodiments, a targeting agent is or is associated with a detectable moiety. In some embodiments, a targeting agent is associated with a therapeutic moiety.

Identification and/or Characterization of Agents that Target Lipid Scavenging

In some embodiments, the present disclosure provides methodologies for identification and/or characterization of agents that target lipid scavenging.

For example, as described herein, the present invention provides technologies for assessing lipid scavenging by cells, e.g., tumor cells, for example by determining fatty acid content of cells, and/or taking various lipid and/or metabolite measurements.

In some embodiments, provided systems may be utilized to identify and/or characterize agents that target lipid scavenging.

For example, in some embodiments, overall lipid level, and/or level of one or more particular lipids or lipid types is altered in a cell in the present of an agent that targets lipid scavenging as described herein, as compared with in its absence and/or as compared with a relevant control. In some embodiments, distribution of lipid types (e.g., relative amounts of particular lipid species and/or lipid types) is altered in a cell (e.g., a tumor cell or tumor) in the presence of an agent that targets lipid scavenging as described herein, as compared with in its absence and/or as compared with a relevant control.

In some embodiments, tumor volume is reduced in the presence or an agent that targets lipid scavenging as described herein, as compared with in its absence, and/or as compared with a relevant control.

In some embodiments, a plurality of test agents is provided, whose utility as a lipid scavenging targeting agent as described herein is to be assessed. In some such embodiments, members of such plurality are assayed as described herein, relative to an appropriate control. Such a test agent may be designated as a lipid scavenging targeting agent if its presence or level correlates with a relevant change in a feature of lipid scavenging as described herein, relative to an appropriate reference.

In some embodiments, test agents may be individually subjected to one or more assays or assessments as described herein. In some embodiments, test agents may be pooled together and then subjected to one or more assays or assessments as described herein. Pools so subjected may then be split for further assays or assessments.

In some embodiments, high throughput screening methods are used to screen a chemical or peptide library, or other collection, containing a large number of potential test compounds. Such "chemical libraries" are then screened in one or more assays to identify those library members (particular chemical species or subclasses) that display a desired characteristic activity. Compounds thus identified can serve as conventional "lead compounds" or can themselves be used as potential or actual modulators (e.g., as therapeutics).

Detecting Tumors Susceptible to Treatment by Targeting Lipid Scavenging

As described herein, the present invention provides various methodologies for detecting and/or classifying tumors that are more or less likely to respond to particular types of therapy such as, for example, therapy targeting lipid biosynthesis or therapy targeting lipid scavenging.

In some embodiments, tumors are detected and/or classifying by determining level and/or type of lipid present in tumor cells, for example relevant to an appropriate control (e.g., cells of adjacent non-tumor tissues).

In some embodiments, tumors are detected and/or classified by determining level, amount or type of a feature that correlates with lipid scavenging status. For example, as described herein, the present disclosure demonstrates that Ras-associated tumors are lipid scavenging tumors. Thus, in some embodiments, tumors that are more or less likely to respond to particular types of therapy are identified and/or characterized through determination and/or detection of one or more characteristics of Ras activity and/or of one or more tumor-associated markers whose presence, form or level correlates with lipid scavenging activity.

In some embodiments, tumors are detected and/or classified by detecting and/or quantifying a particular cancer-associated Ras allele (e.g., H-RasV12G, K-RasG12D, and/or K-RasG12V).

Treating Tumors by Targeting Lipid Scavenging

Growth of mammalian cells requires replication of membrane structures. On this basis, there has been interest in treating cancer with inhibitors of fatty acid synthesis enzymes including fatty acid synthase and acetyl CoA carboxylase. Such enzymes produce "non-essential" fatty acids. Replication of lipid structures, however, also requires essential fatty acids, including polyunsaturated fatty acids such as Omega-3 and Omega-6 fatty acids.

As described herein, at least three lines of evidence point to the importance of unsaturated fatty acids for tumor growth. One line involves measurement of the fatty acid composition (total composition, determined by saponifying membrane lipids and triglycerides) of human pancreatic cancer compared to benign adjacent tissue. It was observed that pancreatic cancer is highly enriched in phosphatidylglycerol phospholipids with polyunsaturated fatty acid tails (See FIG. 11). Another line involved measuring the impact of different diets on the growth of a Ras-driven lung cancer. It was observed that the growth of xenografted tumor cells from the Ras-driven lung cancer line A549 is faster in mice fed a diet rich in unsaturated fatty acids compared to mice fed a diet rich in saturated fatty acids or in carbohydrates (which can be metabolized into saturated fatty acids) (See FIG. 12). The third line involved studies of fatty acid uptake from serum by cultured cancer cells (See FIGS. 1-10). Together these data indicate treatment of cancer, e.g., Ras-driven tumors, which are among the most common causes of death by cancer in the United States, by limiting intake of some or all unsaturated fatty acids. In particular, the evidence presented herein points to the importance of limiting uptake of omega-6 fatty acids.

These observations run absolutely counter to current clinical practice. It is very common for patients with cancer to suffer from poor appetite and low body weight. Accordingly, dietitians frequently prescribed fat supplements to help prevent wasting and cachexia. These supplements are typically based on fish oil, which is rich in unsaturated essential fatty acids. Such fatty acids may actually promote tumor growth. Thus an aspect of the present disclosure includes supplements that are depleted in omega-6 fatty acids, or more generally in polyunsaturated fatty acids, or yet more generally in all unsaturated fatty acids. Such supplements do not currently exist, because they would be viewed as problematic from a cardiovascular safety perspective. Nevertheless, such cardiovascular issues are minor concerns to cancer patients as compared to taking all possible dietary and supplementation steps to minimize their cancer.

In general, the present disclosure demonstrates the desirability and effectiveness of treating certain tumors, and in particular Ras-associated tumors, by targeting lipid scavenging. Those skilled in the art will appreciate that any of a variety of approaches may be utilized to effectuate such targeting. In some embodiments (e.g., in certain dietary control embodiments described herein), availability of certain lipids for scavenging is limited, for example by controlling lipid intake in the diet.

In some embodiments, particular components of lipid scavenging machinery are targeted, for example through use of an agent that interacts directly with such component, or otherwise modulates its level and/or activity.

In some embodiments a general lipid scavenging approach is implemented. In some embodiments, steps are taken to target scavenging of particular lipids or lipid types. In some particular embodiments, at least lysophospholipid scavenging is targeted. In some embodiments, scavenging of at least phosphatidylglycerol lipids and/or fatty acids with higher degrees of unsaturation and/or longer carbon chains is targeted. In various embodiments, a therapeutic modality targeting lipid scavenging, including by dietary control, as described herein is administered over a time period of at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, or until a therapeutic endpoint is observed, e.g., tumor shrinkage is observed.

Dietary Control

Among other things, the present disclosure encompasses treatment of certain tumors through modulation of dietary fatty acid intake.

In one aspect, the present disclosure specifically provides modalities for reducing successful lipid scavenging by Ras-driven cells (e.g., Ras-associated tumors) by controlling levels and/or types of scavenged lipids in serum, for example through dietary control of lipid intake. In some embodiments, lipid intake is controlled by limiting intake of favored scavenged lipids. In some embodiments, lipid intake is controlled by regulating relative intake of favored scavenged lipids as compared with other lipids. In some particular embodiments, lipid intake is controlled through provision and/or use of a nutritional supplement comprising lipids, and particular contain lipids that are not favored scavenged lipids for the cells or tumors of interest.

In some particular embodiments, lipid intake is controlled by administering to a patient in need thereof a diet high in saturated fatty acid diet but low in poly-unsaturated fatty acid. In some embodiments, such diet comprises an excess of fully saturated fatty acids and/or is substantially free of polyunsaturated fatty acids. In some embodiments, such diet comprises intake of a nutritional supplement that provides fully saturated fatty acids (e.g., that consists of or comprises such fully saturated fatty acids)

In some embodiments, a desired diet may be achieved by combining a protein-rich supplement with additional supplementation of fats comprising high levels (approximately 100% or more of the recommended daily intake of ~15 g, based on a 2000 calorie diet) of saturated fatty acids, but low levels (approximately 0-50% of the recommended daily intake of approximately 20 g, based on a 2000 calorie diet, e.g., less than 10 g, 8 g, 6 g, 2 g, 1 g, or 0.5 g) of poly-unsaturated fatty acids. A minimum amount of poly-unsaturated fatty acids for preventing malnutrition will vary from person to person and dosing will be corrected by a clinician after assessing occurrence of potential side effects, such as dry, scaly skin, susceptibility to infection, poor wound healing, impaired vision, and neurological abnormalities.

As an alternative to combining the fat supplementation with the above described protein supplements, in some embodiments, fat supplements may be used without additional protein supplementation.

In various embodiments, a nutritional supplement that may be used as part of a useful dietary regimen described herein comprises lipids, wherein a majority of the lipids contain fatty acid tails and wherein the ratio of saturated fatty acids to polyunsaturated fatty acids in the supplement is greater than 1. As used herein, a "majority" means that at least 50.1% of the lipids present in the supplement have a fatty acid tail.

For example, without limitation, one embodiment of the present disclosure includes a nutritional supplement or food substitute in the form of a capsule or a pill, comprising a coating and an interior calorie rich substance, wherein the coating is any pill or capsule coating known in the art and wherein the interior calorie rich substance comprises fatty acids and/or lipids. In some embodiments, the composition of fatty acids and lipids is selected to mitigate the growth of cancer in an individual taking the supplement, for example as compared with taking a comparable (e.g., an otherwise analogous or identical supplement) with alternative fatty acids or lipids, or lacking fatty acids or lipids.

In various aspects, a provided nutritional supplement, food substitute, and/or dietary regimen is selected, designed, and/or manufactured to include fatty acids in a ratio of saturated to (poly)-unsaturated fatty acids greater than 1, 2, 3, 4, 5, 8, 10, 15, 20, 25, 30, 35, 40, 45, or 50. In some embodiments, included fatty acids are obtained from animal and/or plant sources. As will be appreciated by those skilled in the art, various such sources can provide lipids and/or lipid mixtures rich in saturated fatty acids. In some embodiments, a provided nutritional supplement, food substitute, and/or dietary regimen includes appropriate levels of unsaturated (e.g., poly-unsaturated) fatty acids to meet minimum daily requirements for maintenance of health and/or to achieve a particular desired ratio, for example, of omega-3 to omega-6 fatty acids (e.g, to achieve a desired therapeutic benefit). In various aspects, it is desirable to include omega-3 fatty acids in excess of omega-6 fatty acids, e.g., in a molar ratio greater than 1, 2, 3, 4, 5, 7, 10, 15, 20, 25, or 30. In some embodiments, at least some included fatty acids are obtained from fish or other sources rich in polyunsaturated fatty acids.

In some embodiments, fatty acids included in a provided nutritional supplement, food substitute, and/or dietary regimen are in free fatty acid form; in some embodiments, they are provided as a component of (e.g., in the context of), for example, glycerides and/or phospholipids (e.g., lysophospholipids).

In various embodiments, one or more fatty acids obtained from a source is subjected to hydrogenation prior to inclusion in a nutritional supplement, food substitute, and/or dietary regimen as described herein. Alternatively or additionally, in some embodiments, one or more fatty acids from a first source is combined with one or more fatty acids from a second source to provide a fatty acid composition for use in a nutritional supplement, food substitution, and/or dietary regimen in accordance with the present invention.

In some embodiments, the total fat content of a nutritional supplement, food substitute and/or dietary regimen as utilized in accordance with the present invention is at least 10%, 20%, 30%, 40%, 50%, 60%, 70%, 80%, 90%, or 100% or more of the recommended daily intake of ~15 g (based on a 2000 calorie diet) of saturated fatty acids, and approximately 0%, 10%, 20%, 30%, 40%, or 50% of the recommended daily intake of approximately 20 g (based on a 2000 calorie diet) of poly-unsaturated fatty acids.

In some embodiments, a desired level of fatty acid ingestion is achieved by consuming by 1-5 unit doses of a nutritional supplement or food substitute as described herein. For example, in some embodiments, a utilized nutritional supplement or food substitute contains a weight ratio of saturated to polyunsaturated fatty acids of 10:1 (e.g., 10 g of saturated fatty acids and 1 g of polyunsaturated fatty acids, or analogously 10 g of lipids rich in saturated fatty acids and 1 g of lipid rich in polyunsaturated fatty acids). In some embodiments, such nutritional supplement or food substitutes are included in a dietary regimen that is otherwise low in fat; optionally, such diet may also be low in protein.

In some embodiments, a nutritional supplement, food substitute and/or dietary regimen utilized in accordance with the present invention has an arachidonic acid concentration less than 1.0% by weight, less than 0.9% by weight, less than 0.8% by weight, less than 0.7% by weight, less than 0.6% by weight, less than 0.5% by weight, less than 0.4% by weight, less than 0.3% by weight, less than 0.2% by weight, less than 0.1% by weight, or less than 0.05% by weight.

In some embodiments, a nutritional supplement, food substitute and/or dietary regimen utilized in accordance with the present invention is at least 30%, at least 40%, at least 50%, at least 60%, or at least 70% lipid by weight.

In general, a nutritional supplement and/or food substitute utilized in accordance with the present invention, may be manufactured, provided, and/or utilized in any form known in the art, such as a powder, a gel, a suspension, a paste, a solid, a liquid, a liquid concentrate, a reconstituteable powdered milk substitute or a ready-to-use product. In some embodiments, such a nutritional supplement and/or food substitute is standardized to a specific caloric content, is provided as a ready-to-use product, and/or is provided in a concentrated form. In various embodiments, the composition is in powder form, for example with a particle size in the range of 5 μm to 1500 μm.

Fatty acids are utilized in accordance with the present invention in purified, encapsulated and/or chemically or enzymatically-modified form, for example selected, provided, and/or manufactured so as to deliver the desired sensory and stability properties. In some embodiments, encapsulated fatty acids resist dissolution with water but are released upon reaching the small intestine. In some embodiments, such result can be achieved through use of, for example, an enteric coating, such as cross-linked alginate, and/or by other approaches known and/or routinely practiced in the art.

In some embodiments, a nutritional supplement, food substitute and/or dietary regimen utilized comprises a protein source. In some embodiments, a protein source may be any protein source known in the art, including without limitation, milk (e.g., nonfat milk), whey protein, casein, soy protein, hydrolyzed protein, and amino acids. In some embodiments, bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g., sodium caseinate, sodium calcium caseinate, calcium caseinate) and combinations thereof.

In various embodiments, proteins are provided, manufactured, and/or utilized in accordance with the present invention as intact proteins. In various embodiments, proteins are provided, manufactured, and/or utilized as a combination of both intact proteins and partially hydrolyzed proteins, for example with a degree of hydrolysis of between about 4% and 10%. In various embodiments, proteins are more completely hydrolyzed. In various embodiments, a protein source provided, manufactured, and/or utilized in accordance with the present invention consists of or comprises individual amino acids and/or short oligopeptides.

In various embodiments, a composition (e.g., a nutritional supplement and/or a food substitute) utilized in accordance with the present invention to support a desired dietary regimen includes saturated and unsaturated fatty acids from various sources, in free form and/or as part of lipid structures, sugar, water, glucose, gelatin, citric acid, natural flavors, glazing agent (including, but without limitation, palm oil, white beeswax, carnauba wax, emulsifier: glycerol esters), tartaric acid, ascorbyl palmitate, malic acid, colors added (including, without limitation, curcumin, paprika, and other coloring agents).

In various embodiments, an exemplary such composition includes saturated fatty acids from various sources known in the art, in free form and/or as part of lipid structures, gelatin, glycerin, water, natural lemon oil, mixed natural tocopherols as preservative.

Combination Therapy

In some embodiments, modalities that target lipid scavenging as described herein are combined with one or more other therapies in the treatment of cancer, e.g., of Ras-associated cancer.

Various poly-unsaturated fatty acids, and especially the ω-6 fatty acid arachidonic acid have been implicated in the promotion of breast and pancreatic tumor growth, as well as other types of cancer. Whereas the exact mechanisms by which poly-unsaturated fatty acids promote tumor growth remain unknown, it was shown that in pancreatic cancer it may depend on the arachidonic metabolizing enzyme cyclooxygenase-2 (Funahashi et al, Pancreas, 2008). This may explain why NSAID usage may be associated with a lower incidence of pancreatic cancer and potentially other cancers (Bradley et al, B. J. Cancer, 2010). Therefore, diet modulated to contain high levels of saturated fatty acids (100% of the recommended daily intake or higher), but low levels of the poly-unsaturated fatty acid arachidonic and potentially other poly-unsaturated fatty acids (0-50% of the recommended daily intake), synergize with the NSAIDs class of drugs or other cyclooxygenase inhibitors.

In various embodiments, provided modalities for targeting lipid scavenging are administered to a cancer patient during a chemotherapeutic regimen. In some embodiments, such a chemotherapeutic regimen can comprise administration of any chemotherapeutic agent known in the art. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above.

Pharmaceutical Compositions

In accordance with various embodiments of methods of the invention, an agent that targets lipid scavenging and/or a lipid for ingestion as part of a dietary regimen or supplement, can be administered to a subject alone, or as a component of a composition or medicament, as described herein. In some embodiments, a provided agent or lipid can be formulated with a physiologically acceptable carrier or excipient to prepare a pharmaceutical composition. In some embodiments, a carrier utilized in such a pharmaceutical compositions, and/or the composition itself, can be sterile. In some embodiments, a pharmaceutical composition is formulated for a specific mode of administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. In some embodiments, pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

A composition or medicament, if desired, can contain one or more of protein (esp. albumin), nanoparticles, microparticles, liposomes, and micelles, for example as carriers, particularly for delivery of fatty acids and/or lipids.

A composition or medicament, if desired, can contain (typically minor amounts of) wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

In some embodiments, a utilized composition or medicament provided, manufactured, and/or utilized in accordance with the present invention, includes both a therapeutic agent (e.g., a chemotherapeutic agent) and one or more fatty acids. In some such embodiments, the composition of medicament contains fatty acid types and/or amounts as otherwise described herein.

A composition or medicament can be formulated in accordance with routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, an agent as described herein may be provided as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A composition described herein may be administered by any appropriate route. In some embodiments, a composition is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a composition is administered intravenously. In some embodiments, a composition is administered orally. In some embodiments, a composition is administered by direct administration to a target tissue, such as heart or muscle (e.g., intramuscular), tumor (intratumorallly), nervous system (e.g., direct injection into the brain; intraventricularly; intrathecally). Alternatively or additionally, a composition can be administered by inhalation, parenterally, intradermally, transdermally, or transmucosally (e.g., orally or nasally). More than one route can be used concurrently, if desired.

In some embodiments, a composition is administered in a therapeutically effective amount and/or according to a dosing regimen that is correlated with a particular desired outcome.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an agent or lipid is administered at a therapeutically effective amount. In some such embodiments, a "therapeutically effective amount" may be determined, for example, with consideration of total amount of the agent or lipid included in a particular composition. In some embodiments, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a particular tumor or tumor.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

In some embodiments, a formulation comprising an agent or lipid described herein administered as a single dose. In some embodiments, such a formulation is administered at regular intervals. Administration at an "interval," as used herein, indicates that the therapeutically effective amount is administered periodically (as distinguished from a one-time dose). The interval can be determined by standard clinical techniques. In some embodiments, a formulation is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an agent or lipid described herein is administered at regular intervals indefinitely. In some embodiments, such a formulation is administered at regular intervals for a defined period. In some embodiments, a formulation is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

EXAMPLES

The following examples are provided for illustration and are not in any way to limit the scope of the invention.

Example 1: Hypoxic and Ras-Transformed Cells Support Growth by Scavenging Unsaturated Fatty Acids from Lysophospholipids Materials and Methods Cell Culturing, SCD1 Inhibition, and Lipid Supplementation:

Cell lines were from ATCC with the following exceptions: the immortalized Baby Mouse Kidney (iBMK) cell lines were derived from primary kidney epithelial cells from Bax$^{-/-}$/Bak$^{-/-}$ mice, immortalized by E1A and dominant-negative p53 expression, and transfected with control vector, human oncogenic H-Ras$^{V12G}$, or myrAKT (31); and the Human Pancreatic Nestin Expressing (HPNE) cells (a generous gift of A. Maitra) were developed from human pancreatic duct by transduction with a retroviral expression vector (pBABEpuro) containing the hTERT gene and transfected with control vector or human oncogenic K-Ras$^{G12D}$. Cell lines were routinely passaged in Dulbecco's Modified Eagle Medium (DMEM, Mediatech) with 25 mM glucose and 4 mM glutamine and supplemented with 10% Fetal Bovine Serum (HyClone), 25 IU/ml penicillin, and 25 µg/ml streptomycin (MP Biomedicals) and split at 80% confluence. Metabolic experiments were performed in 6 cm culture dishes with 3 ml of DMEM containing 10% dialyzed serum (DFBS, HyClone). For isotope labeling, glucose and glutamine were replaced with their U-$^{13}$C-labeled forms (Cambridge Isotope Labs). Hypoxia experiments were performed in a hypoxic glove box (0.5% or 1% $O_2$ as indicated, 5% $CO_2$ and 94-94.5% $N_2$, 37° C.) (Coy Laboratory Products). Cells and media were equilibrated in low oxygen overnight before experiment initiation. CAY10566 was from Cayman Chemical. Lipid supplements were from Avanti Polar Lipids. LPC(18:1) and LPC(18:0) were dissolved in phosphate buffered saline (PBS); MG(18:1) in methanol; and PC(16: 0-18:1) in 1:9 chloroform:methanol. Organic solvents were <0.1% v/v in the medium.

Cell Proliferation Assays and Tumor Xenograft Studies:

Cell proliferation was determined with either Packed Cell Volume tubes (PCV, Techno Plastic Products AG) or with the xCELLigence system (Roche). Animal studies were performed following the guidelines for proper and humane use of animals in research under an IACUC-approved protocol. To generate allografts, 1×10$^7$ iBMK cells were implanted in matrigel (BD Biosciences) into nu/nu athymic female mice. After establishment of palpable tumors, mice were randomized to receive 2.5 mg/kg BID CAY10566 p.o. in 0.5% methylcellulose or vehicle control. Xenograft tumors were measured biweekly and tumor volume calculated as volume=(length×width$^2$×π/6).

Lipid and Metabolite Measurements:

For saponified fatty acid analysis from cells, media was aspirated, cells rinsed twice with 2 ml room temperature PBS, 1 ml 50:50 MeOH/H$_2$O solution with 0.1M HCl at −20° C. added, and the resulting liquid and cell debris scraped into a microfuge tube. For analogous measurements from media, 0.5 ml medium was mixed with 0.5 mL MeOH with 0.2 M HCl. Chloroform (0.5 mL) was added, the mixture vortexed for 1 min and then centrifuged at 16,000×g for 5 min, and the chloroform layer transferred to a glass vial. The extract was dried under $N_2$, reconstituted into 90:10 MeOH/H$_2$O containing 0.3 M KOH, incubated at 80° C. for 1 h to saponify fatty acids, acidified with 0.1 ml of formic acid, extracted twice with 1 ml hexane, dried under $N_2$, and reconstituted into 1:1:0.3 MeOH:chloroform:H$_2$O (1 ml solvent per 2 µl packed volume for cells, and 2 ml solvent total for the media samples) for LC-MS analysis. Separation was by reversed-phase ion-pairing chromatography on a C8 column coupled to negative-ion mode full-scan LC-MS at 1 Hz scan time and 100,000 resolving power (stand-alone orbitrap, Thermo Fischer Scientific).

For medium lipid analysis, the dried chloroform extract from 0.5 ml medium was obtained as above, reconstituted in 0.3 ml 1:1:0.3 MeOH:chloroform:H$_2$O and analyzed by LC-MS as above. For analysis of free (non-esterified) fatty acids, 1 ml medium was extracted three times with 1 ml ethyl acetate and the extract dried and reconstituted in 0.5 ml 1:1:0.3 MeOH:chloroform:H$_2$O. For analysis of water soluble metabolites, media was aspirated from the cells and metabolism quenched immediately 80:20 MeOH/H$_2$O at −80° C. The resulting liquid and cell debris were then scraped into a microfuge tube and extracted three times with 80% MeOH at −80° C., the extract dried under $N_2$, reconstituted into H$_2$O (50 µl/µl cell volume), and analyzed by LC-MS as above except using a C18 column. Medium glucose and lactate concentrations were measured with an YSI7200 electrochemical analyzer (YSI). Oxygen consumption was determined using a Seahorse XF24 flux analyzer (Seahorse Bioscience).

Results

The Source of Cellular Fatty Acids can be Probed with 13C-Labeled Glucose and Glutamine:

Mammalian cells acquire fatty acids either through uptake or de novo synthesis (FIG. 1A). Fatty acid synthase makes the saturated fatty acid palmitate (C16:0), which can be desaturated and/or elongated to make a diversity of fatty acids. The metabolic routes to such fatty acids can be probed by supplying uniformly $^{13}$C-labeled glucose and glutamine (to label acetyl-CoA) and subsequent mass spectrometry analysis of saponified fatty acids. For palmitate, such analysis reveals an unlabeled fraction (M$^0$ peak) due to import of serum-derived fatty acids, as well as labeled forms arising from de novo lipogenesis. These labeled forms include U-$^{13}$C-palmitate (M$^{+16}$) and partially labeled forms which arise due to incomplete acetyl-CoA labeling (FIG. 1B), with the relative abundance of the partially and fully labeled forms sufficient to determine the fractional labeling of cytosolic acetyl-CoA. Applying this approach to five cancer cell lines with diverse origins demonstrates that, in line with previous findings, in normoxic conditions de novo lipogenesis accounts for 75-90% of the cellular C16:0 pool (FIG. 1C) (30).

In normoxia, glucose is the primary source for lipogenic acetyl-CoA. In contrast, in hypoxia (0.5-1% $O_2$), pyruvate dehydrogenase is less active. In such conditions, an increased fraction of citrate and thus acetyl-CoA is produced through glutamine-driven reductive carboxylation (FIG. 1D). Consistent with this, when U-$^{13}$C-glucose or U-$^{13}$C-glutamine tracers are supplied separately, it was determined that glucose-derived carbon is the predominant acetyl-CoA source in normoxia, whereas glutamine-derived carbon contributes more in hypoxia (FIG. 1E).

Hypoxic Cells Bypass SCD1 by Importing Fatty Acids:

The most abundant fatty acid in mammalian cells is oleate (C18:1), the main product of stearoyl-CoA desaturase 1 (SCD1). The SCD1-catalyzed reaction is oxygen-dependent and therefore it was hypothesized that it might be slowed in hypoxia (FIG. 2A). To explore the effect of hypoxia on fatty acid synthesis, elongation, and desaturation, we simultaneously fed U-$^{13}$C-glucose and U-$^{13}$C-glutamine to hypoxic cells, and observed that fatty acid labeling was decreased compared to normoxia, with increased unlabeled (M$^0$) peaks indicative of enhanced fatty acid import from serum (FIG. 2B, S1). Consistent with impaired SCD1 activity, the decrease in labeling was particularly profound for the monounsaturated fatty acids C18:1 (FIG. 2B, S1). This decreased C18:1 labeling is associated also with an overall change in cellular lipid composition, in the direction of saturated fatty acids (lower C18:1/C18:0 ratio, or "desaturation index", FIG. 2C). Thus, cellular lipid composition per se is impacted by hypoxia, indicating that import is insufficient to fully compensate for the impaired SCD1 activity.

In cells fed U-$^{13}$C-glucose and U-$^{13}$C-glutamine, C16:0 elongation to C18:0 usually adds labeled carbon. Thus, the only major route to unlabeled C18:0, which is modestly increased in hypoxia (FIG. 2D), is import from serum. In contrast, in addition to direct uptake, unlabeled C18:1 can arise from desaturation of unlabeled C18:0 (FIG. 2A). To confirm that SCD1 activity is decreased in hypoxia, the labeling data (where L equals the fraction of a given fatty acid that is labeled) was used to calculate D, the fraction of C18:1 made by SCD1. Fractional import/equals 1−D. Since serum fatty acids are not labeled, the only route to labeled C18:1 is desaturation of labeled C18:0:

$$L_{C18:1} = (D)(L_{C18:0}) \tag{Eqn. 1}$$

$$D = L_{cell\ C18:1}/L_{cell\ C18:0} \tag{Eqn. 2}$$

It was determined that D is indeed decreased, and thus C18:1 import increased, in hypoxia (FIG. 2E).

Oncogenic Ras Recapitulates Hypoxic Metabolism:

In addition to the effects of hypoxia, the contribution of specific oncogenes to the balance between de novo lipogenesis and fatty acid import was examined. Like hypoxia, oncogenic Akt and Ras have been implicated in increasing glucose uptake in transformed cells. While the PI3K-Akt pathway has been shown to promote lipogenesis, the impact of Ras on fatty acid metabolism has not previously been well studied. Therefore, fatty acid metabolism in an isogenic cellular model system was examined: immortalized Baby Mouse Kidney (iBMK) cells with no oncogene (CTL), membrane-targeted and thus activated Akt (myrAkt), or oncogenic H-Ras (H-Ras$^{V12G}$). Introduction of myrAkt resulted in increased de novo synthesis of monounsaturated (but not saturated) fatty acids as evidenced by an increased desaturation index (C18:1/C18:0) and decrease in the fraction of monounsaturated fatty acids coming from import (FIGS. 3A & 3B, Figure S2). In contrast, oncogenic H-Ras$^{V12G}$ caused a decrease in the desaturation index, indicating that Ras and Akt activation lead to fundamentally different cellular lipid composition. In addition, oncogenic H-Ras$^{V12G}$ increased the fraction of cellular fatty acids acquired via import. This was most pronounced for C18:1, implying reduced SCD1 flux. The increased utilization of serum-derived fatty acids by Ras-driven cells was confirmed by direct measurements of fatty acid uptake from medium (FIG. 3C).

To examine the generality of the impact of oncogenic Ras on monounsaturated fatty acid uptake, human pancreatic nestin expressing (HPNE) cells with no oncogene (CTL) or oncogenic K-Ras (K-Ras$^{G12D}$) were used. Like oncogenic H-Ras$^{V12G}$ in iBMK cells, expression of oncogenic K-Ras$^{G12D}$ in HPNE cells led to a lower desaturation index, more incorporation of serum C18:1 into cellular lipids, and faster serum C18:1 uptake (FIG. 3D-F).

We next examined the impact of Ras versus Akt on other metabolic parameters impacted by hypoxia: glucose uptake, lactate excretion, oxygen consumption, and glutamine metabolism. In iBMK cells, both oncogenic Ras and Akt caused an increase in glucose uptake and increased shunting of glucose-derived carbon towards lactate (FIG. 3G). However, while Akt-transformed cells maintained oxygen consumption at levels comparable to control cells, Ras-transformed cells displayed a significant decrease in oxygen consumption, and increased fractional contribution of reductive carboxylation flux to citrate synthesis, as evidenced by increased $^{13}C_5$-labeled citrate in cells fed U-$^{13}C$-glutamine (FIG. 3H-I) (33). Similar results were observed in K-Ras$^{G12D}$ transformed HPNE cells (FIG. 3J-L). Taken together, these results demonstrate that oncogenic Ras has an opposite effect to Akt with respect to regulation of fatty acid metabolism in general and SCD1 flux in particular, and that it recapitulates a metabolic phenotype of hypoxic cells. Thus, among other things, the present disclosure demonstrates that therapeutic modalities targeting fatty acid metabolism, and particularly those targeting SCD1, may not be effective, at least not alone, for treatment of certain Ras-associated tumors, even though they may be useful and/or effective when used to treat other cancers (e.g., AKt-associated tumors). On the flip side, the present disclosure demonstrates that therapeutic modalities targeting lipid import may be particularly effective for treatment of certain Ras-associated tumors.

Oncogenic Ras Confers Resistance to SCD1 Inhibition:

SCD1 inhibition can block the growth of cancer cells, both in vitro and in xenografts. In experiments with A549 lung cancer cells, however, an SCD1 inhibitor dose (200 nM CAY10566) that completely blocked C18:1 labeling (FIG. 4A), did not impair cell growth in a real-time cell proliferation assay (10% serum, FIG. 4B) or for the first 48 h of growth in standard cell culture conditions (Figure S3). Consistent with the persistent cell growth being supported by serum lipids, switching to 2% serum rendered the cells sensitive to SCD1 inhibition (FIG. 4B). Since A549 cells naturally express oncogenic K-Ras, and Ras promotes C18:1 uptake, it was hypothesized that constitutive Ras activation might induce resistance to SCD1 inhibition. To explore this, iBMK cells with H-Ras$^{V12G}$ or myrAkt in the presence of SCD1 inhibitor were grown. The inhibitor fully blocked SCD1 in both cell lines (Figure S4). Nevertheless, in 10% serum, while growth of myrAkt cells was severely impaired, the H-Ras$^{V12G}$ cells grew almost normally for 3 population doublings (FIG. 4C, Figure S3). These data again confirm that, as demonstrated herein, therapeutic modalities targeting fatty acid metabolism, and particularly those targeting SCD1, may not be effective, at least not alone, for treatment of certain Ras-associated tumors, even though they may be useful and/or effective when used to treat other cancers (e.g., AKt-associated tumors).

To determine robustness against SCD1 inhibition in vivo, athymic nude mice were injected with iBMK cells with myrAkt or H-Ras$^{V12G}$. After establishment of palpable tumors, the mice were treated with vehicle or SCD1 inhibitor (2.5 mg/kg CAY10566 p.o. BID). The effect of SCD1 inhibition on the Akt-driven tumors was greater than on the Ras-driven tumors (FIG. 4D,E), with the mean tumor volume at day 13 or 14 post therapy, relative to untreated tumors, 0.51+/−0.04 and 0.67+/−0.05 respectively (p=0.01 for Ras-Akt comparison, by two-tailed T-test). Thus, oncogenic Ras (at least relative to activated Akt) confers resistance to SCD1 inhibition, both in vitro and in allografts.

Imported Fatty Acids Originate from Lysophospholipids:

Results described herein demonstrate, among other things, that oncogenic Ras increases import of exogenous fatty acids, conferring resistance against SCD1 inhibition. While free (non-esterified) fatty acids have been shown to rescue cell proliferation during SCD1 inhibition when supplemented in large enough quantities, their levels in serum are insufficient to account for the observed fatty acid uptake and associated cell growth (Table 2).

TABLE 2

| A | Medium total fatty acids | Medium free fatty acids | A549 total fatty acids | iBMK-H-Ras$^{V12G}$ total fatty acids |
|---|---|---|---|---|
| | μM | | nmol/μl cell | |
| 16:0 | 22.3 ± 1.5 | 0.85 ± 0.08 | 8.7 ± 0.5 | 8.1 ± 0.6 |
| 16:1 | 5.1 ± 0.5 | n.a | 3.3 ± 0.2 | 2.2 ± 0.6 |
| 18:0 | 12.2 ± 0.3 | 0.25 ± 0.08 | 2.8 ± 0.3 | 4.4 ± 0.08 |
| 18:1 | 20.9 ± 0.9 | 1.1 ± 0.04 | 10.5 ± 0.3 | 8.1 ± 0.2 |

Total and free (non-esterified) fatty acid concentrations in medium (10% serum), and total fatty acid concentrations in A549 and iBMK-H-RAS$^{V12G}$ cells. Medium free fatty acids constitute less than 5% of total medium fatty acids.

To identify which lipids were the source for the scavenged fatty acids, glycerophospholipid levels by mass spectrometry in fresh and spent medium were profiled (FIG. 5A). The levels of typical glycerophospholipids (i.e., glycerol with a head group and two fatty acid tails) did not change substantially. However, a near total depletion of the glycerophospholipids with only one fatty acid tail was observed (lysophospholipids, FIG. 5B). The selective lysophospholipid depletion was observed for all cell lines tested (Figure S5A).

Lysolipids Support Growth of Ras-Driven Cells:

Quantitative analysis of lysolipid uptake suggests that LPC(18:1) plays a significant role in meeting cellular demand for monounsaturated fatty acids: In iBMK-H-Ras$^{V12G}$ cells treated with SCD1 inhibitor, the uptake of LPC(18:1) over 48 hours was comparable to the total cellular C18:1 incorporation during this time period (FIG. 3C, S3, S5) and depletion of serum LPC(18:1) occurred simultaneous with growth inhibition (Figure S3, S5).

To further evaluate LPC(18:1) as a nutrient, the medium of the iBMK cells was spiked with 20 μM LPC(18:1), half the concentration found in 100% serum (i.e. physiological conditions). The desaturation index (C18:1/C18:0), initially more than two-fold higher in iBMK-myrAkt cells than iBMK-H-Ras$^{V12G}$ cells, increased significantly and selectively in iBMK-H-Ras$^{V12G}$ cells upon addition of LPC(18:1) (FIG. 5C). This coincided with the fraction of C18:1 derived from import, while increasing for both cell lines with LPC(18:1) addition, being more than twice as high in iBMK-H-Ras$^{V12G}$ cells (FIG. 5D). Consistent with a differential dependency on SCD1 relative to C18:1 import, LPC(18:1) supplementation during SCD1 inhibition fully restored proliferation for iBMK-H-Ras$^{V12G}$ cells but only partially for iBMK-myrAkt cells (FIG. 5E, F). Similarly, a complete rescue was observed for the Ras-driven A549 human cancer cell line (FIG. 5G).

The analysis of serum lipid consumption suggested that lysolipids provide a more accessible nutrient source than serum glycerophospholipids. Consistent with this, in SCD1 inhibitor-treated cells, supplementation with PC(16:0,18:1) did not restore cell growth (FIG. 5E). A possible explanation is the presence also of the saturated tail (C16:0). Indeed, supplementation with saturated lysolipid LPC(18:0) caused stronger growth inhibition than SCD1 inhibition alone. However, simultaneous incubation with LPC(18:1) and LPC(18:0) restored growth, proving that the growth restoration with LPC(18:1) but not PC(16:0,18:1) reflects greater cellular access to the lysolipid's monounsaturated fatty acid tail. Consistent with lysolipids being preferred substrates for fatty acid scavenging, oleolyl-monoacylglycerol, MG(18:1), also restored cell proliferation. Thus, lysolipid scavenging can meet cellular monounsaturated fatty acid needs.

Among other things, these finding demonstrate that treatment of at least some Ras-associated tumors might well benefit from depriving or limiting access of such tumors (e.g., via dietary control or other means) to certain types of lipids, and particularly to lipids that could be scavenged by tumor cells. In some embodiments, such depriving or limiting access comprises reducing exposure to favored scavenged lipids and/or providing increased exposure to alternative, non-favored scavenged lipids. For example, in some embodiments, access to polyunsaturated lipids is limited; in some particular embodiments, access to lysolipids is limited, for example in favor of glycerophospholipids.

In some particular embodiments, lipid access is limited through control of dietary intake.

In some embodiments, relevant useful dietary control comprises intake of an excess of fully saturated fatty acids, for example relative to polyunsaturated fatty acids and in some embodiments to the substantial exclusion of such polyunsaturated fatty acids. In some embodiments, relevant, relevant useful dietary control comprises avoiding lysolipids, for example in favor of glycerophospholipids.

Discussion

Tumors require fatty acids to replicate their cellular membranes and thereby grow. It is commonly assumed that cancer cells synthesize most of their non-essential fatty acids de novo. This assumption is based primarily on cell culture experiments conducted in 10% serum and normoxia. It is supported by the glucose-dependent pro-lipogenic effects of one of the most important oncogenic pathways, PI3K-Akt-mTOR. Because Ras activates Akt (3, 36), it has been thought that Ras might also have a glucose-dependent pro-lipogenic role.

However, as demonstrated herein, we have identified the source of a problem in such assumptions, For example, we demonstrate that Ras does not induce glucose-dependent de novo lipogenesis, but instead stimulates scavenging of serum fatty acids. Such scavenging is an intrinsic property of all cells we studied, and is further increased by Ras activation, hypoxia, and addition to media of physiological concentrations of lysophospholipid (i.e., phospholipids with only one fatty acid tail). Enhanced scavenging can render Ras-driven cells resistant to pharmacological inhibition of the main mammalian desaturase, SCD1. Moreover, it may facilitate the growth of Ras-driven tumors in hypoxic conditions by circumventing SCD1, which requires molecular oxygen as an electron acceptor.

Both Ras activation and hypoxia, in addition to inducing fatty acid scavenging, also increase the fraction of acetyl-CoA units produced from glutamine. Moreover, Ras activation leads to decreased oxygen consumption. Without wishing to be bound by any particular theory, the present disclosure proposes that one possible source of the metabolic parallels between hypoxia and Ras activation might be that both Ras and hypoxia activate HIF (or both converge on another signaling protein) (37), which in turn produces the observed metabolic commonalities. Another is that Ras activation, like hypoxia, directly impairs oxidative phosphorylation, leading to increased NADH (or another metabolite), which in turn leads to the lipid metabolic changes. In support of this latter possibility, Ras has recently been shown to migrate to the mitochondrion and inhibit complex I (21).

The key substrates of the fatty acid scavenging pathway are serum lysophospholipids. In contrast to standard phospholipids with two tails, lysophospholipids provide a readily accessible fatty acid source for cells. For example, oleoyl lysophosphatidylcholine, but not a corresponding phosphatidylcholine species with two fatty acid tails, rescues cells from SCD1 inhibition. While free oleate (C18:1) can also rescue cells from SCD1 inhibition, lysophospholipids are more abundant than free fatty acids in serum, and thus likely a more important physiological source. For example, about 20% of serum oleate is in the form of oleoyl lysophosphatidylcholine compared to 5% in the free fatty acid form.

The mechanism by which cells scavenge lysophospholipids is not fully established. Intriguingly, the enzyme monoacylglycerol lipase (MAGL), which generates free fatty acids from monoacylglycerols, is highly expressed in aggressive cancer cells and its over-expression enhances tumorigenicity (26). Its expression is also increased by the H-Ras and the K-Ras-HIF pathways (27, 28). While it has been previously hypothesized that the relevance of MAGL to cancer is via enhancing the levels of pro-tumorigenic lipid messengers such as lysophosphatidic acid and PGE2, the present disclosure proposes that it may also contribute to lysolipid scavenging.

The present disclosure teaches that uptake and utilization of lysophospholipids by Ras-driven cells may be part of a more global "scavenger" lifestyle. Oncogenic Ras up-regulates both autophagy and macropinocytosis, both involving uptake of bulk material into endocytic vesicles (22-24). The former consumes intracellular contents (cellular cannibalism) and the latter extracellular ones. Both can provide nutrition via macromolecule degradation, and it is possible that macropinocytosis contributes directly to lysolipid uptake.

Irrespective of a potential role for macropinocytosis, scavenging is a metabolic hallmark of Ras driven cancers. While tumors driven by the PI3K-Akt pathway wantonly engage in biosynthesis and become metabolically vulnerable (38), the present disclosure teaches that those driven primarily by oncogenic Ras instead have the capacity to maintain rapid growth by utilizing extracellular macromolecules to obtain the required substrates for new macromolecule and lipid production. This finding has therapeutic implications, rendering Ras driven tumors comparatively robust to inhibitors of anabolic enzymes such as SCD1. At the same time, it teaches that scavenging pathway enzymes may be therapeutic targets for Ras-driven cancers. The present invention therefore provides various methods of identifying and/or characterizing therapeutic modalities effective for the treatment of Ras-associated cancers, including by disruption of one or more features of macromolecular scavenging. The present invention also provides methods of treating Ras-associated cancers with such therapeutic modalities.

Example 2: Fatty Acid Content of Pancreatic Tumor Tissue as Compared with Benign Adjacent Tissue The present Example describes analysis of lipid abundance in paired samples of pancreatic ductal adenocarcinoma tumor and benign adjacent tissues.

Specifically, paired pancreatic ductal adenocarcinoma tumor and benign adjacent tissue specimens were acquired by surgical resection from 20 patients. The sample collection protocol was designed to minimize metabolic changes: During surgery, effort was taken to maintain tissue and tumor perfusion until just prior to excision, after which tumor and benign adjacent tissue samples were rapidly submersed into liquid nitrogen, stored at $\leq -70°$ C., extracted in parallel, and analyzed by LC-MS.

Figure 11:
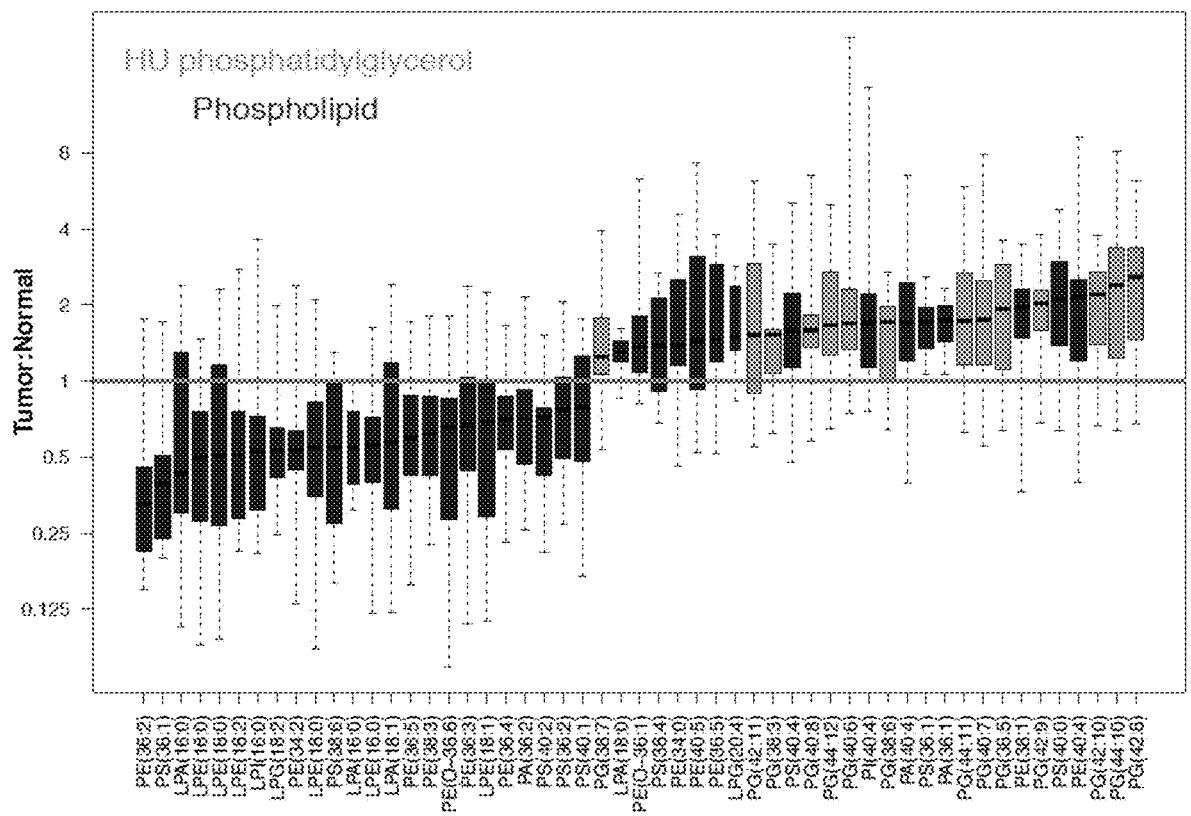
FIG. 11. Lipid tumor/benign adjacent ratios in human pancreatic cancer. Relative ratios of lipid abundances in human pancreatic tumor tissues were compared to benign adjacent tissue from the same patients. Values are averages of 20 patient, and $p<0.05$ with correction for multiple hypothesis testing. Abbreviations: PE, phosphatidylethanolamine; PS, phosphatidylserine; PG, phosphatidylglycerol; PC, phosphatidylcholine; L, lysophospholipid. Larger numbers refer to the total number of carbon atoms in the fatty acid tails of the lipid; smaller numbers refer to the degree of unsaturation. O-refers to an ether lipid.
Figure 12:
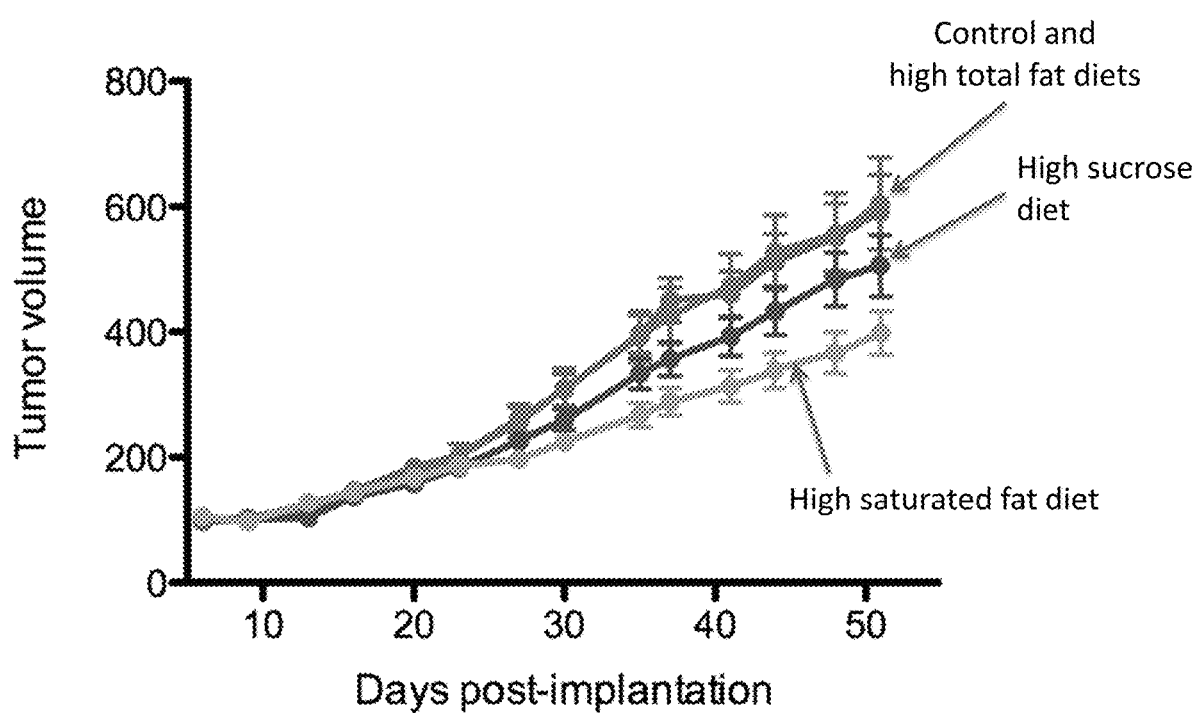
FIG. 12. A549 Xenografts. Growth curves of xenografted A549 (Ras-driven lung cancer) cells in athymic nude mice, fed on control, high total fat, high sucrose, or high saturated fat diets were performed. Values are average of 5 mice±SEM.

The relative ratios of lipid abundances in human pancreatic tumor tissues were compared to benign adjacent tissue from the same patients. Results are presented in FIG. 11. Although error bars overlap, FIG. 11 illustrates a notable segregation of those species significantly observed in each type of tissue. Furthermore, FIG. 11 shows, among other things, that phosphatidylglycerol lipids were detected in tumor tissues and not in the benign adjacent tissues. Also, fatty acids with higher degrees of unsaturation tended were much more likely to be found in tumor tissues than in the benign adjacent tissues. Longer chain fatty acids appeared more prevalent in tumor as compared with benign tissues; for example, in the studies whose results are depicted in FIG. 11, no species with a carbon length longer than 40 was observed predominantly in benign tissues. Combining these observations, phosphatidylglycerol lipids containing fatty acids with high degrees of unsaturation were high in tumor tissues compared to the benign adjacent tissues, whereas lysophospholipids were relatively depleted.

Thus, in some embodiments, the present invention provides methods and technologies for treating Ras-associated cancers by depriving tumor cells of access to phosphatidylglycerol lipids and/or to fatty acids with high degrees of unsaturation and/or longer carbon chains (e.g., greater than 40). The present invention also provides methods of identifying and/or characterizing effective therapeutic modalities for the treatment of Ras-associated tumors by identifying and/or characterizing agents that disrupt scavenging (e.g., import) of such phosphatidylglycerol lipids and/or to fatty acids with high degrees of unsaturation and/or longer chains into tumor cells.

In some particular embodiments, access of tumor cells to their preferred scavengeable fatty acids (i.e. phosphatidylglycerol lipids, fatty acids with high degrees of unsaturation, and/or longer chain fatty acids, and particularly to phosphatidylglycerol lipids containing fatty acids with high degrees of unsaturation), can be impacted via dietary control. For example, in some embodiments, subjects suffering from or susceptible to Ras-associated tumors are administered a diet low in phosphatidylglycerol lipids and/or in fatty acids with high degrees of unsaturation and/or longer chain fatty acids. In some embodiments, subjects suffering from or susceptible to Ras-associated tumors are administered a diet relatively low in phosphatidylglycerol lipids and/or to fatty acids with high degrees of unsaturation and/or longer chain fatty acids as compared with other lipid sources (e.g., as compared with fully saturated fatty acids).

In many embodiments, limiting access of tumor cells to their preferred scavengeable fatty acids comprises providing alternative lipid sources, for example that consist of or comprise fully saturated fatty acids. In some embodiments, subjects are administered a diet that comprises an excess of fully saturated fatty acids. In some embodiments, subjects are administered a diet that comprises an excess of fully saturated fatty acids relative to polyunsaturated fatty acids and/or particularly as compared to phosphatidylglycerol lipids.

Example 3: Effect of Dietary Control

The present Example demonstrates effects of certain dietary programs on growth of Ras-associated tumors.

Specifically, growth characteristics of xenografted A549 (Ras-driven lung cancer) cells in athymic nude mice fed on control, high total fat, high sucrose, or high saturated fat diets were determined. Results are presented in FIG. 12. As can be seen, tumors grew fastest in mice fed on diets containing abundant unsaturated fatty acids (control and high total fat diets) grow fastest, whereas feeding of a diet highly enriched in saturated fatty acids slows tumor growth.

The present disclosure therefore teaches that control of dietary fatty acid intake can impact growth of certain tumors, and particularly certain Ras-associated tumors. In some embodiments, provided treatment modalities for such tumors include restricting unsaturated fatty acids and/or supplementing saturated fatty acids in diet of the subject suffering from or susceptible to a relevant cancer.

REFERENCES

1. DeBerardinis R J, Sayed N, Ditsworth D, Thompson C B (2008) Brick by brick: metabolism and tumor cell growth. *Curr Opin Genet Dev* 1854-61.
2. Vander Heiden M G, Cantley L C, Thompson C B (2009) Understanding the Warburg effect: The metabolic requirements of cell proliferation. *Science* 324(5930):1029-1033.

3. Shaw R J & Cantley L C (2006) Ras, PI(3)K and mTOR signalling controls tumour cell growth. *Nature* 441424-430.
4. Gingras A-C, Raught B, Sonenberg N (2001) Regulation of translation initiation by FRAP/mTOR. *Genes Dev* 15807-826.
5. Luyimbazi D et al. (2010) Rapamycin regulates stearoyl CoA desaturase 1 expression in breast cancer. *Mol Cancer Ther* 9(10):2770-2784.
6. Menendez J A & Lupu R (2007) Fatty acid synthase and the lipogenic phenotype in cancer pathogenesis. *Nat Rev Cancer* 7763-777.
7. Kim J-W, Tchernyshyov I, Semenza G L, Dang C (2006) HIF-1-mediated expression of pyruvate dehydrogenase kinase: a metabolic switch required for cellular adaptation to hypoxia. *Cell Metab* 3(3):177-185.
8. Papandreou I, Cairns R A, Fontana L, Lim A L, Denko N C (2006) HIF-1 mediates adaptation to hypoxia by actively downregulating mitochondrial oxygen consumption. *Cell Metab* 3(3):187-197.
9. Metallo C M et al. (2011) Reductive glutamine metabolism by IDH1 mediates lipogenesis under hypoxia. *Nature* 481(7381):380-384.
10. Wise D R et al. (2011) Hypoxia promotes isocitrate dehydrogenase-dependent carboxylation of α-ketoglutarate to citrate to support cell growth and viability. *Proc Natl Acad Sci USA* 108(49):19611-19616.
11. Mullen A R et al. (2011) Reductive carboxylation supports growth in tumour cells with defective mitochondria. *Nature* 481(7381):385-388.
12. Guillou H, Zadravec D, Martin P G P, Jacobsson A (2010) The key roles of elongases and desaturases in mammalian fatty acid metabolism: insights from transgenic mice. *Prog Lipid Res* 49186-199.
13. Hess D, Chisholm J W, Igal R A (2010) Inhibition of stearoylCoA desaturase activity blocks cell cycle progression and induces programmed cell death in lung cancer cells. *PLOS One* 5(6):e11394.
14. Green C D & Olson L K (2011) Modulation of palmitate-induced endoplasmic reticulum stress and apoptosis in pancreatic β-cells by stearoyl-CoA desaturase and Elovl6. *Am J Physiol Endocrinol Metab* 300E640-E649.
15. Hardy S, Langelier Y, Prentki M (2000) Oleate activates phosphatidylinositol 3-kinase and promotes proliferation and reduces apoptosis of MDA-MB-231 breast cancer cells, whereas palmitate has opposite effects. *Cancer Res* 606353-6358.
16. Miyazaki M et al. (2009) Stearoyl-CoA desaturase-1 deficiency attenuates obesity and insulin resistance in leptin-resistant obese mice. *Biochem Biophys Res Commun* 380818-822.
17. Roongta U V et al. (2011) Cancer cell dependence on unsaturated fatty acids implicates stearoyl-CoA desaturase as a target for cancer therapy. *Mol Cancer Res* 9(11):1551-1561.
18. Igal A R (2011) Roles of stearoylCoA desaturase-1 in the regulation of cancer cell growth, survival and tumorigenesis. *Cancers* 32462-2477.
19. Mason P et al. (2012) SCD1 inhibition causes cancer cell death by depleting monounsaturated fatty acids. *PLOS One* 7(3):e33823.
20. Ying H et al. (2012) Oncogenic Kras maintains pancreatic tumors through regulation of anabolic glucose metabolism. *Cell* 149656-670.
21. Hu Y et al. (2012) K-ras$^{G12V}$ transformation leads to mitochondrial dysfunction and a metabolic switch from oxidative phosphorylation to glycolysis. *Cell Res* 22399-412.
22. Guo J Y et al. (2011) Activated Ras requires autophagy to maintain oxidative metabolism and tumorigenesis. *Genes Dev* 25(5):460-470.
23. Yang S et al. (2011) Pancreatic cancers require autophagy for tumor growth. *Genes Dev* 25(7):717-729.
24. Bar-Sagi D & Feramisco J. R. (1986) Induction of membrane ruffling and fluid-phase pinocytosis in quiescent fibrblasts by Ras proteins. *Science* 233(4768):1061-1068.
25. Kalaany N Y & Sabatini D M (2009) Tumours with PI3K activation are resistant to dietary restriction. *Nature* 458725-732.
26. Nomura D K et al. (2010) Monoacylglycerol lipase regulates a fatty acid network that promotes cancer pathogenesis. *Cell* 14049-61.
27. Chun S Y et al. (2010) Oncogenic KRAS modulates mitochondrial metabolism in human colon cancer cells by inducing HIF-1α and HIF-2α target genes. *Mol Cancer* 9293-304.
28. Joyce T, Cantarella D, Isella C, Medico E, Pintzas A (2009) A molecular signature for epithelial to mesemchymal transition in a human colon cancer cell system is revealed by large-scale microarray analysis. *Clin Exp Metastasis* 26569-587.
29. Kamphorst J J, Fan J, Lu W, White E, Rabinowitz J D (2011) Liquid chromatography-high resolution mass spectrometry analysis of fatty acid metabolism. *Anal Chem* 83(23):9114-9122.
30. Kannan R, Lyon I, Baker N (1980) Dietary control of lipogenesis in vivo in host tissues and tumors of mice bearing Ehrlich ascites carcinoma. *Cancer Res* 404606-4611.
31. Degenhardt K & White E (2006) A mouse model system to genetically dissect the molecular mechanisms regulating tumorigenesis. *Clin Cancer Res* 12(18):5298-5304.
32. Degenhardt K, Chen G, Lindsten T, White E (2002) BAX and BAK mediate p53-independent suppression of tumorigenesis. *Cancer Cell* 2193-203.
33. Gaglio D et al. (2011) Oncogenic K-Ras decouples glucose and glutamine metabolism to support cancer cell growth. *Mol Syst Biol* 7523-538.
34. Krypuy M, Newnham G M, Thomas D M, Conron M, Dobrovic A (2006) High resolution melting analysis for the rapid and sensitive detection of mutations in clinical samples: KRAS codon 12 and 13 mutations in non-small cell lung cancer. *BMC Cancer* 6295-307.
35. Sasagawa T, Okita M, Murakami J, Kato T, Watanabe A (1998) Abnormal serum lysophospholipids in multiple myeloma patients. *Lipids* 34(1):17-21.
36. Khwaja A, Rodriguez-Viciana P, Wennstrom S, Warne P H, Downward J (1997) Matrix adhesion and Ras transformation both activate a phosphoinositide 3-OH kinase and protein kinase B/Akt cellular survival pathway. *EMBO J* 16(10):2783-2793.
37. Sheta E A, Trout H, Gildea J J, Harding M A, Theodorescu D (2001) Cell density mediated pericellular hypoxia leads to induction of HIF-1alpha via nitric oxide and Ras/MAP kinase mediated signaling pathways. *Oncogene* 20(52):7624-7634.
38. Schulze A & Harris A L (2012) How cancer metabolism is tuned for proliferation and vulnerable to disruption. *Nature* 491364-373.

39. Lu W et al. (2010) Metabolomic analysis via reversed-phase ion-pairing liquid chromatography coupled to a stand alone orbitrap mass spectrometer. *Anal Chem* 823212-3221.

What is claimed is:

1. A method for inhibiting growth of a Ras-driven cancer cell or hypoxic cell, the method comprising contacting the cell with one or more saturated fatty acids, wherein contacting the cell with one or more saturated fatty acids comprises administering a nutrient with an excess of saturated fatty acids relative to polyunsaturated fatty acids.

2. The method of claim 1, wherein the polyunsaturated fatty acids in the nutrient comprise one or more omega-3 fatty acids.

3. The method of claim 1, wherein the nutrient comprises a ratio of saturated fatty acids to polyunsaturated fatty acids of at least 30:1.

4. The method of claim 1, wherein the nutrient comprises a ratio of saturated fatty acids to polyunsaturated fatty acids of at least 50:1.

5. The method of claim 1, wherein the cell is a pancreatic cancer cell.

6. The method of claim 1, wherein the cell is a lung cancer cell.

7. The method of claim 1, wherein the cell is a hypoxic cell.

8. The method of claim 1, wherein the cell is a cancer cell.

9. The method of claim 1, wherein contacting the cell with one or more saturated fatty acids comprises contacting the cell with one or more lipids comprising one or more saturated fatty acid tails.

10. The method of claim 9, wherein each of one or more of the lipids comprises a plurality of fatty acid tails.

11. The method of claim 9, wherein the one or more lipids comprise phosphatidylcholine lipids.

12. The method of claim 11, wherein the phosphatidylcholine lipids are PC (16:0, 18:1) lipids.

13. The method of claim 9, wherein the one or more lipids comprise saturated lysolipids.

14. The method of claim 13, wherein the saturated lysolipids are LPC (18:0) lipids.

15. The method of claim 1, wherein the polyunsaturated fatty acids in the nutrient comprise omega-3 fatty acids in excess of omega-6 fatty acids.

16. The method of claim 1, wherein the nutrient comprises a ratio of saturated fatty acids to polyunsaturated fatty acids of at least 2:1.

17. The method of claim 1, wherein the nutrient comprises a ratio of saturated fatty acids to polyunsaturated fatty acids of at least 10:1.

* * * * *